(12) United States Patent
Chen

(10) Patent No.: US 11,020,612 B2
(45) Date of Patent: Jun. 1, 2021

(54) METHOD AND EYE MASK APPARATUS FOR TREATING AN EYE USING A BROAD AREA LIGHT SOURCE

(71) Applicant: Iridex Corporation, Mountain View, CA (US)

(72) Inventor: Howard Chen, San Jose, CA (US)

(73) Assignee: IRIDEX Corporation, Mountain View, CA (US)

(*) Notice: Subject to any disclaimer, the term of this patent is extended or adjusted under 35 U.S.C. 154(b) by 377 days.

(21) Appl. No.: 15/892,893

(22) Filed: Feb. 9, 2018

(65) Prior Publication Data
US 2018/0229051 A1    Aug. 16, 2018

Related U.S. Application Data

(60) Provisional application No. 62/459,466, filed on Feb. 15, 2017, provisional application No. 62/516,478, filed on Jun. 7, 2017.

(51) Int. Cl.
| | | |
|---|---|---|
| *A61F 9/008* | (2006.01) | |
| *A61N 5/06* | (2006.01) | |
| A61N 5/067 | (2006.01) | |

(52) U.S. Cl.
CPC ......... *A61N 5/0625* (2013.01); *A61N 5/0613* (2013.01); *A61F 2009/00891* (2013.01);
(Continued)

(58) Field of Classification Search
CPC .... A61F 9/007; A61F 9/00781; A61F 9/0079; A61F 9/008; A61F 9/00821; A61F 2009/00861; A61F 2009/00863; A61F 2009/00891; A61N 5/06; A61N 5/0613; A61N 5/0626; A61N 5/0642; A61N 5/0643; A61N 5/0644; A61N 5/0645; A61N 5/0648; A61N 5/065; A61N 5/0651; A61N 5/0652; A61N 5/0665; A61N 5/066; A61N 5/067; A61N 2005/0626;
(Continued)

(56) References Cited

U.S. PATENT DOCUMENTS

| | | |
|---|---|---|
| 3,034,403 A | 5/1962 | Neefe |
| 4,576,453 A | 3/1986 | Borowsky |

(Continued)

FOREIGN PATENT DOCUMENTS

DE    3535072 A1    4/1987

*Primary Examiner* — Ahmed M Farah
(74) *Attorney, Agent, or Firm* — Kilpatrick Townsend & Stockton LLP

(57) ABSTRACT

A light based system for treating an eye includes a mask that is configured for positioning on the eye and a light source that is configured to deliver therapeutic light. The mask has an inner surface that is positionable against the eye and an outer surface that is opposite the inner surface. The mask is optically opaque to prevent transmission of light through the mask and the mask includes at least one transparent opening that allows transmission of light through the mask to target tissue of the eye posterior the transparent opening. The light source is positioned relative to the mask so that the delivered therapeutic light irradiates at least a portion of the mask and the transparent opening. Therapeutic light traverses through the transparent opening to the target tissue positioned posterior the transparent opening.

14 Claims, 9 Drawing Sheets

(52) U.S. Cl.
CPC .............. *A61N 2005/067* (2013.01); *A61N 2005/0626* (2013.01); *A61N 2005/0644* (2013.01); *A61N 2005/0648* (2013.01); *A61N 2005/0652* (2013.01); *A61N 2005/0666* (2013.01)

(58) Field of Classification Search
CPC .... A61N 2005/0642; A61N 2005/0643; A61N 2005/0644; A61N 2005/0645; A61N 2005/0648; A61N 2005/065; A61N 2005/0651; A61N 2005/0652; A61N 2005/0665; A61N 2005/0666; A61N 2005/067
USPC .............. 606/3, 4–6, 10–12; 607/88–92, 108
See application file for complete search history.

(56) References Cited

U.S. PATENT DOCUMENTS

| | | | |
|---|---|---|---|
| 4,732,148 A * | 3/1988 | L'Esperance, Jr. | A61F 9/00804 606/5 |
| 4,732,715 A | 3/1988 | Bawa et al. | |
| 4,966,452 A | 10/1990 | Shields et al. | |
| 5,108,388 A * | 4/1992 | Trokel | A61F 9/008 606/13 |
| 5,135,466 A | 8/1992 | Fedorov et al. | |
| 5,147,284 A | 9/1992 | Fedorov et al. | |
| 5,376,086 A | 12/1994 | Khoobehi et al. | |
| 5,434,630 A | 7/1995 | Bransome | |
| 5,697,923 A * | 12/1997 | Poler | A61F 9/008 606/4 |
| 5,719,656 A | 2/1998 | Bowling | |
| 6,520,956 B1 * | 2/2003 | Huang | A61F 9/008 606/10 |
| 6,874,886 B2 | 4/2005 | Miller et al. | |
| 7,321,795 B2 | 1/2008 | Bogdanowicz | |
| 7,564,014 B2 * | 7/2009 | Huh | A61F 9/067 2/8.1 |
| 7,727,138 B2 | 6/2010 | Alvarado | |
| 8,070,688 B2 | 12/2011 | Livne et al. | |
| 8,287,592 B2 | 10/2012 | Silvestrini | |
| 8,308,292 B2 | 11/2012 | Arai et al. | |
| 8,527,055 B2 | 9/2013 | Rickard | |
| 8,914,089 B2 | 12/2014 | Abreu | |
| 9,138,142 B2 | 9/2015 | Christie et al. | |
| 9,144,376 B2 | 9/2015 | Guth et al. | |
| 2003/0109907 A1 | 6/2003 | Shadduck | |
| 2004/0043351 A1 | 3/2004 | Logan et al. | |
| 2005/0003322 A1 | 1/2005 | Logan et al. | |
| 2005/0033420 A1 * | 2/2005 | Christie | A61F 2/14 623/5.12 |
| 2006/0271026 A1 * | 11/2006 | Silvestrini | A61B 3/0091 606/4 |
| 2010/0076419 A1 | 3/2010 | Chew et al. | |
| 2011/0137303 A1 | 6/2011 | Dolleris et al. | |
| 2011/0137307 A1 | 6/2011 | Imran | |
| 2012/0209356 A1 * | 8/2012 | Eckhouse | G02C 7/16 607/88 |
| 2013/0060306 A1 * | 3/2013 | Colbauch | A61N 5/0618 607/88 |
| 2013/0123761 A1 | 5/2013 | Belkin et al. | |
| 2014/0192311 A1 | 7/2014 | Pletcher et al. | |
| 2015/0238357 A1 | 8/2015 | Goldberg et al. | |
| 2015/0366706 A1 | 12/2015 | Belkin et al. | |
| 2015/0374539 A1 | 12/2015 | Buzawa et al. | |
| 2016/0192988 A1 | 7/2016 | Albright | |
| 2017/0007834 A1 | 1/2017 | Irazoqui et al. | |
| 2017/0087014 A1 | 3/2017 | Potter et al. | |
| 2018/0000337 A1 | 1/2018 | Chen et al. | |

* cited by examiner

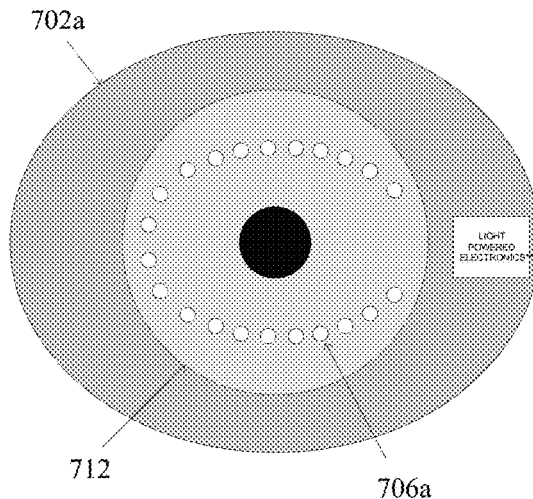
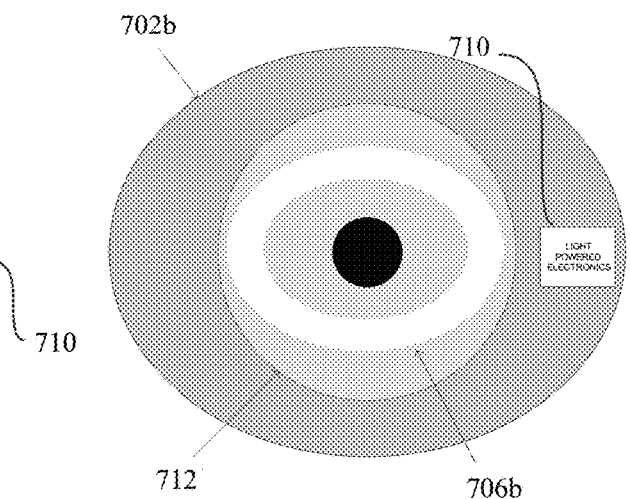
Figure 14       Figure 15
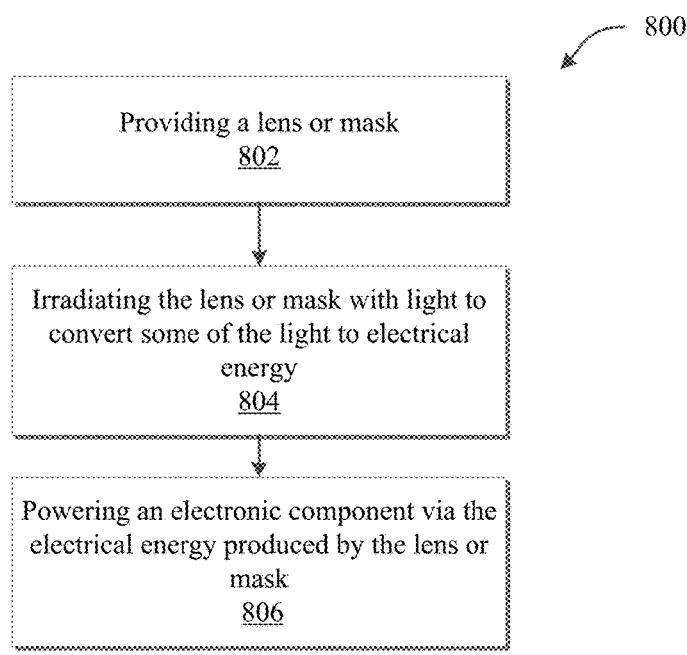
Figure 16

METHOD AND EYE MASK APPARATUS FOR TREATING AN EYE USING A BROAD AREA LIGHT SOURCE

CROSS-REFERENCE TO RELATED APPLICATIONS

This Application claims priority to Provisional U.S. Patent Application No. 62/459,466 filed Feb. 15, 2017, entitled "Method and Eye Mask Apparatus for Treating an Eye Using a Broad Area Light Source" and Provisional U.S. Patent Application No. 62/516,478 filed Jun. 7, 2017, entitled "Method and Eye Mask Apparatus for Treating an Eye Using a Broad Area Light Source." The entire disclosure of both aforementioned Provisional U.S. Patent Applications are hereby incorporated by reference, for all purposes, as if fully set forth herein. This Application is also related to Provisional U.S. Patent Application No. 62/459,487 filed Feb. 15, 2017, entitled "Method and Apparatus for Cyclo-Scanner Using Surface Emitting Lasers or LEDs" and entitled "Method and Apparatus for Cyclo-Scanner Using Surface Emitting Laser or Leds", filed concurrently herewith and to the same Assignee, the entire contents of which are incorporated by reference herein for all purposes.

BACKGROUND OF THE DISCLOSURE

The present disclosure is generally related to medical systems, devices, and methods for treating a glaucomatous eye. Glaucoma is a leading cause of blindness. Glaucoma involves the loss of retinal ganglion cells in a characteristic pattern of optic neuropathy. Untreated glaucoma can lead to permanent damage of the optic nerve and resultant visual field loss, which can progress to blindness. The loss of visual field due to glaucoma often occurs gradually over a long time and may only be recognized when the loss is already quite advanced. Once lost, this damaged visual field can never be recovered.

Elevated intraocular pressure (IOP) is a significant risk factor for developing glaucoma. IOP is a function of production of aqueous humor by the ciliary body of the eye and its drainage through the trabecular meshwork and all other outflow pathways including the uveoscleral pathway. Aqueous humor is a complex mixture of electrolytes, organics solutes, and other proteins that supply nutrients to the non-vascularized tissues of the anterior chamber of the eye. It flows from the ciliary bodies into the posterior chamber, bounded posteriorly by the lens and the ciliary zonule and bounded anteriorly by the iris. Aqueous humor then flows through the pupil of the iris into the anterior chamber, bounded posteriorly by the iris and anteriorly by the cornea. In the conventional aqueous humor outflow path, the trabecular meshwork drains aqueous humor from the anterior chamber via Schlemm's canal into scleral plexuses and the general blood circulation. In open angle glaucoma there is reduced flow through the trabecular meshwork. In angle closure glaucoma, the iris is pushed forward against the trabecular meshwork, preventing the egress of fluid.

Uveoscleral outflow is a non-conventional pathway that is gaining importance in the management of glaucoma. In uveoscleral outflow, aqueous humor enters the ciliary muscles from the anterior chamber and exits through the supraciliary space and across the anterior or posterior sclera. Uveoscleral outflow may contribute significantly to total aqueous humor outflow.

Currently, glaucoma therapies aim to reduce IOP by either limiting the production of aqueous humor or by increasing the outflow of aqueous humor. Medications such as beta-blockers, carbonic anhydrase inhibitors, etc., are used as the primary treatment to reduce the production of aqueous humor. Medications may also be used as the primary therapy to increase the outflow of the aqueous humor. Miotic and cholinergic drugs increase the trabecular outflow, while prostaglandin drugs, for example, Latanoprost and Bimatoprost, increase the uveoscleral outflow. These drugs, however, are expensive and have undesirable side effects, which can cause compliance-dependent problems over time.

Surgery may also be used to increase the outflow or to lower the production of aqueous humor. Laser trabeculoplasty is the application of a laser beam over areas of the trabecular meshwork to increase the outflow. Cyclocryotherapy and laser cyclophotocoagulation are surgical attempts to lower the production of aqueous humor by the ciliary processes. Although they may be effective, these destructive surgical interventions are normally used as a last resource in the management of glaucoma due to the risk of the severe complication of phthisis bulbi. Other adverse side effects of cyclodestructive surgical procedures may include ocular hypotony and inflammation of the anterior eye segment, which may be associated with an increased incidence of macula complications. Still other adverse side effects include transient hyphaema and exudates in the anterior chamber, uveitis, visual loss, and necrotizing scleritis.

In laser transscleral cyclophotocoagulation, high intensity continuous wave (CW) infrared laser energy is directed through selected portions of the pars plicata region to the ciliary body, structures under the scleral layers and the overlying conjunctiva. Selected portions of the ciliary body and related processes are permanently destroyed, thereby decreasing the overall production of aqueous humor. Laser energy may be directed through air to a patient seated at a special slit lamp. Alternatively, laser energy may be delivered through the use of fiber optic handpieces placed in contact with the patient's eyeball. In both laser energy delivery methods, however, accurately and repeatedly directing a laser beam to a subsurface non-visible target such as the ciliary body can be challenging for a surgeon.

Conventional laser based surgical system use a single light source such as an edge emitting diode laser, diode pumped solid state laser, or fiber laser to treat glaucoma conditions. In such conventional systems, the light from a laser is transported by an optical waveguide (e.g., multi-mode fiber probe) to the site of the treatment in an eye. The probe used for glaucoma treatment typically touches the surface of the eye, with the laser source releasing pulsed energy at a target or treatment spot. The probe is then moved to a different target or treatment spot, typically in a clockwise or counterclockwise rotation around the edge of the eye, and the probe is then used again to release pulsed energy at the new target or treatment spot. This process is commonly referred to as "cyclo photocoagulation" for treating an eye.

While the prior systems, methods, and devices have provided advancements in the art, there is a need for improved systems that are less dependent on a physician or operator positioning and that are less dependent on expensive light sources and/or complex optical systems.

SUMMARY OF THE DISCLOSURE

Embodiments of the present disclosure generally relate to ophthalmic laser treatment systems. In some embodiments, the ophthalmic laser treatment systems may include a lens or eye mask that is positioned atop the eye and a light source that is configured to deliver therapeutic light toward the eye mask and eye. In certain embodiments, the ophthalmic laser treatment systems may be used to provide treatment that is similar to cyclophotocoagulation of the eye of a patient for the treatment of glaucoma.

The lens or eye mask provides several advantages over conventional systems including the use of broad area light sources, which results in less reliance on traditional laser consoles, traditional treatment probes, and/or expensive optical waveguides, aiming beams, laser collimation devices, etc. The use of the broad area light sources and lens or eye mask may greatly reduce manufacturing and/or treatment costs. In addition, the lens or eye mask may provide more consistent, reliable, and safer treatment applications that are less dependent on a health care professional (HCP) for precise alignment and control of a treatment beam of light.

According to one aspect, a light based system for treating an eye of a patient includes an eye mask, such as a contact lens, that is configured for positioning on the eye of the patient. The eye mask has an inner surface that is positionable against the eye and an outer surface that is opposite the inner surface. The eye mask is optically opaque and reflective so that light that contacts the eye mask is reflected away from the outer surface of the eye mask. The eye mask includes at least one transparent opening that allows light to traverse through the eye mask. The transparent opening is positioned about the eye mask so that when the eye mask is positioned on the eye of the patient, the transparent opening is positioned radially outward of a limbus of the eye.

The system also includes a light source that is configured to deliver therapeutic light toward the eye mask. The light source is positioned relative to the eye mask so that the light source irradiates at least a portion of the eye mask and the transparent opening so that a portion of the therapeutic light traverses through the transparent opening to target tissue within the eye. In one embodiment, the transparent opening includes a plurality of openings in which each opening is positioned radially outward relative to the limbus of the eye. In such embodiments, the light source typically irradiates the plurality of openings simultaneously. The eye mask may include between 1 and 100 openings, and more commonly between 5 and 40 openings, and each opening may have an opening diameter of between 1 micron and 1000 microns, between 10 microns and 1000 microns, and more commonly between 50 microns and 600 microns. In other embodiments, the transparent opening is an elongate or annular slot that is positioned radially outward relative to the limbus of the eye. In such embodiments, the light source typically irradiates the entire area of elongate or annular slot. In some embodiment, the transparent opening includes a converging optical element (e.g., a miniature ball lens) or a diverging optical element (e.g., a miniature concave lens) and/or a non-beam-forming material.

The system may further include a spacer that is positioned between the eye mask and the light source in order to separate the eye mask from the light source. The spacer has a proximal end and a distal end that is opposite the proximal end. The proximal end may be coupleable with the light source and the distal end may be aligned with, or positioned atop, the eye mask. The spacer includes a transparent material (such as free-space) that exposes the eye mask to the therapeutic light that is delivered from the light source.

The eye mask typically includes a reflective material that is positioned on the outer surface of the eye mask and that reflects light away from the outer surface of the eye mask. The eye mask may be made of a transparent material and may be rendered opaque due to the reflective material that is positioned on the outer surface of the eye mask. In such embodiments, the plurality of openings may be etched or otherwise formed in the reflective material.

The system may additionally include a control unit that is operably coupled with the light source to control the delivery of therapeutic light to the target tissue of the eye in an automated manner. The control unit may be configured to control the light source to deliver a series of pulses of the therapeutic light to the target tissue with each pulse of the series being sufficient to induce therapeutic healing of the target tissue without causing traditional photocoagulation of the target tissue. The description of each pulse being sufficient to induce therapeutic healing without causing traditional photocoagulation means that no visible damage is present on, or associated with, the target tissue, such as blanching of target tissue. In other embodiments, the control unit may be configured to control the light source to deliver a single pulse of flash of the therapeutic light to the target tissue with the single pulse or flash being sufficient to induce therapeutic healing of the target tissue. The light source may have a curved configuration that corresponds to a curvature of the eye so that the therapeutic light enters the eye at an angle relatively normal to a surface of the eye. For example, an incidence angle of the therapeutic light may be within +/−10 degrees of normal. The light source may be a broad area light source, such as a VCSEL, an LED, and the like.

The outer surface of the eye mask may include a material that is configured to convert light to electrical power (e.g., a solar cell material) so that the therapeutic light that is incident on the outer surface of the eye mask is converted to electrical energy. The material that is configured to convert light to electrical power may cover at least 50 percentage of the surface area of the mask. The eye mask may also include an electronic component that is powered via the electrical power produced by the solar cell material. The electronic component may be a sensor, a MEMS mirror, a wireless signal transceiver, a power detector, or any other electronic component. The mask may further include a passive or active optical component that is embedded in the at least one transparent opening. The passive or active optical component may interact with the therapeutic light that is transmitted through the at least one transparent opening.

In some embodiments, a reflective material may be positioned within the at least one transparent opening of the mask to reflect the therapeutic light transmitted through the at least one opening at an angle for ophthalmological treatment of the tissue positioned posterior of the eye mask. The reflective material may be deposited on an inner surface of the at least one transparent opening or may be disposed within a lens component that is positioned within the at least one transparent opening. The lens component may be an active component in which a relative position of the reflective material within the at least one transparent opening is adjustable. The adjustable active component may the angle of the reflected therapeutic light to be adjusted in order to ensure that the desired tissue within the eye is targeted. In some embodiments, the reflective material is disposed at a pre-selected angle within the at least one transparent opening. The pre-selected angle may be selected so that the reflected therapeutic light is incident on the Schlemm's canal. The angle of the reflected therapeutic light may be greater than 30 degrees and in some embodiments may be between 30 and 120 degrees.

According to another aspect, a light based system for treating glaucoma in an eye of a patient includes a lens that is configured for positioning on the eye of the patient. The lens has an inner surface that is positionable against the eye and an outer surface that is opposite the inner surface. The lens is optically opaque in order to prevent transmission of light through the lens. The lens includes at least one transparent opening that allows transmission of light through the lens to target tissue of the eye positioned posterior the transparent opening. The system also includes a light source that is configured to deliver therapeutic light. The light source is positioned relative to the lens so that the delivered therapeutic light irradiates at least a portion of the lens and the transparent opening so that therapeutic light traverses through the transparent opening to the target tissue positioned posterior the transparent opening.

In some embodiments, the transparent opening includes a plurality of transparent openings that allow the therapeutic light to traverse through the lens. In such embodiments, when the lens is positioned on the eye, each opening of the plurality of transparent openings is positioned radially outward of a limbus of the eye. In other embodiments, the transparent opening is an elongate or annular slot. In such embodiments, when the lens is positioned on the eye, the elongate or annular slot is positioned radially outward of a limbus of the eye.

The outer surface of the lens is typically reflective so that therapeutic light that contacts the optically opaque outer surface of the lens is reflected away from the outer surface. The system may also include a spacer that is positioned between the lens and the light source in order to separate the lens from the light source. The spacer has a proximal end and a distal end that is opposite the proximal end. The proximal end is coupleable with the light source and the distal end is positioned atop the lens.

The system may further include a control unit that is operably coupled with the light source to control the delivery of therapeutic light to the target tissue of the eye in an automated manner. In one embodiment, the control unit may be configured to control the light source to deliver a series of pulses of the therapeutic light to the target tissue with each pulse of the series being sufficient to induce therapeutic healing of the target tissue without causing traditional photocoagulation of the target tissue. In another embodiment, the control unit may be configured to control the light source to deliver a single pulse or flash of the therapeutic light to the target tissue with the single pulse being sufficient to induce therapeutic healing of the target tissue.

According to another aspect, a method for treating glaucoma in an eye of a patient using a light based system includes positioning a mask on a surface of the eye, aligning a light source relative to the mask, and delivering therapeutic light from the light source toward the mask. The mask includes an inner surface and an outer surface that is opposite the inner surface. The mask is optically opaque to prevent transmission of light through the mask. The mask also includes at least one transparent opening that allows transmission of light through the optically opaque mask to target tissue of the eye that is positioned posterior the transparent opening. The therapeutic light is delivered from the light source and toward the mask in order to irradiate at least a portion of the optically opaque mask and the transparent opening so that at least some of the therapeutic light traverses through the transparent opening to the target tissue that is positioned posterior the transparent opening.

Aligning the light source relative to the mask may include positioning a spacer between the mask and the light source to separate the mask from the light source. The spacer may have a proximal end and a distal end that is opposite the proximal end with the proximal end being coupleable with the light source and the distal end being positioned atop the mask. The method may further include activating a control unit in order to deliver the therapeutic light from the light source in an automated fashion. In one embodiment, delivering the therapeutic light from the light source in an automated fashion includes delivering a series of pulses of the therapeutic light to the target tissue with each pulse of the series being sufficient to induce therapeutic healing of the target tissue without causing traditional photocoagulation of the target tissue. In another embodiment, delivering the therapeutic light from the light source in an automated fashion includes delivering a single pulse or flash of the therapeutic light to the target tissue with the single pulse or flash of therapeutic light being sufficient to induce therapeutic healing of the target tissue.

In some embodiments, the mask includes a reflective material that is positioned on the outer surface of the mask and that reflects light away from the outer surface of the mask. The transparent opening may include a plurality of openings and delivering the therapeutic light from the light source may be done so as to simultaneously irradiate each opening of the plurality of openings. Simultaneously irradiating each opening of the plurality of openings may effect a treatment of the eye similar to a cyclophotocoagulation laser treatment. In other embodiments, the transparent opening may be an elongate or annular slot and the therapeutic light may be delivered from the light source to irradiate an entire area of the elongate or annular slot.

According to yet another aspect, a mask (e.g., a contact lens) for treating an eye of a patient is provided. The mask is positionable on the eye of the patient and includes an inner surface that is positionable against the eye and an outer surface that is opposite the inner surface. The mask is optically opaque to prevent transmission of light through the mask. The mask also includes at least one transparent opening that allows transmission of light through the mask to target tissue of the eye positioned posterior of the at least one transparent opening. The outer surface of the mask includes a material that is configured to convert light to electrical power so that light that is incident on the outer surface of the mask is converted to electrical energy. The size of the eye mask is typically large enough to cover the sclera area of the eye and as a result the mask will not be moved relative to the cornea once it is inserted.

The mask is a component of a system that also includes a light source that is configured to deliver therapeutic light. The light source is positioned relative to the mask so that the delivered therapeutic light irradiates at least a portion of the mask and the at least one transparent opening such that therapeutic light traverses through the at least one transparent opening to the target tissue positioned posterior the transparent opening. The light source may be a broad area light source, such as a VCSEL or an LED. The system may also include a spacer that is positioned between the mask and the light source to separate the mask from the light source. The spacer may have a proximal end and a distal end that is opposite the proximal end. The proximal end may be coupleable with the light source and the distal end may be in alignment with the mask. The spacer may include a transparent material (such as free-space) that exposes at least a portion of the mask to the therapeutic light that is delivered from the light source.

The system may also include a control unit that is operably coupled with the light source to control the delivery of therapeutic light to the target tissue of the eye in an automated manner. The control unit may be configured to control the light source to deliver a series of pulses of the therapeutic light to the target tissue with each pulse being sufficient to induce therapeutic healing of the target tissue without causing traditional photocoagulation of the target tissue. In other embodiments, the control unit may be configured to control the light source to deliver a single pulse or flash of the therapeutic light to the target tissue. The single pulse or flash of the therapeutic light may be sufficient to induce therapeutic healing of the target tissue.

The material that is configured to convert light to electrical power may be a solar cell material. The mask may also include an electronic component that is powered via the electrical power produced by the mask. The electronic component may be a sensor, a MEMS mirror, a wireless signal transceiver, a power detector, and the like. The mask may additionally include a passive or active optical component that is embedded in the at least one opening to interact with the light that is transmitted through the at least one opening. The material that is configured to convert light to electrical power covers at least 50 percentage of the surface area of the mask.

In some embodiments the mask includes a plurality of transparent openings (e.g., between 1 and 100 openings and more commonly between 5 and 40 openings). In such embodiments, each opening may be positioned radially outward relative to the limbus of the eye and the light source may simultaneously irradiate each opening. Each opening may have an opening diameter of between 1 and 1000 microns, between 10 and 1000 microns, and more commonly between 100 and 600 microns. In other embodiments, the transparent opening may be an elongate or annular slot that is positioned radially outward relative to the limbus of the eye. The light source may irradiate a portion of the elongate or annular slot or more commonly the entire elongate or annular slot. A reflective material may be positioned on the outer surface of the mask and may reflect light away from the outer surface of the mask. The mask may be made of a transparent material and may be rendered opaque due to the reflective material that is positioned on the outer surface of the mask. In such embodiments, the plurality of openings may be etched or formed in the reflective material.

According to another aspect, a lens for treating an eye of a patient is provided. The lens is positionable on the eye of the patient and includes an inner surface that is positionable against the eye and an outer surface that is opposite the inner surface. The lens also includes a material that is configured to convert light to electrical power so that light that is incident on at least a portion of the lens is converted to electrical energy. The material that is configured to convert light to electrical power covers at least 50 percentage of the surface area of the lens. At least a portion of the lens may be optically opaque to prevent transmission of light through the lens and the material that is configured to convert light to electrical power may be positioned on the optically opaque portion of the lens. The lens also typically includes at least one transparent opening that allows transmission of light through the lens to target tissue of the eye positioned posterior of the at least one transparent opening.

The lens may further include a passive or active optical component that is embedded in the at least one opening to interact with the light that is transmitted through the at least one opening. The lens may additionally include an electronic component that is powered via the electrical power produced by the lens. The electronic component may be a sensor, a MEMS mirror, a wireless signal transceiver, a power detector, and the like.

According to another aspect, a method of converting light energy to electrical power via a lens is provided. The method includes providing a lens that is positionable on an eye, in which the lens includes an inner surface, an outer surface that is opposite the inner surface, and a material that is configured to convert light to electrical power so that light that is incident on at least a portion of the lens is converted to electrical energy. The method also includes irradiating the lens with light so that at least a portion of the light is converted to electrical energy via the material that is configured to convert light to electrical power. The material that is configured to convert light to electrical power covers at least 50 percentage of the surface area of the lens.

At least a portion of the lens is typically optically opaque to prevent transmission of light through the lens and the material that is configured to convert light to electrical power is positioned on the optically opaque portion of the lens. The lens also typically includes at least one transparent opening that allows transmission of light through the lens to target tissue of the eye positioned posterior of the at least one transparent opening. The lens may further include a passive or active optical component that is embedded in the at least one opening to interact with the light that is transmitted through the at least one opening. The lens may additionally include an electronic component that is powered via the electrical power produced by the lens. The electronic component may be a sensor, a MEMS mirror, a wireless signal transceiver, a power detector, and the like.

According to another aspect, a mask (e.g., a contact lens) for treating an eye of a patient is provided. The mask is positionable on the eye of the patient and includes an inner surface that is positionable against the eye and an outer surface that is opposite the inner surface. The mask is optically opaque to prevent transmission of light through the mask and the mask includes at least one transparent opening that allows transmission of light through the mask to tissue of the eye positioned posterior of the mask. The mask also includes a reflective material that is positioned within the at least one transparent opening to reflect light that is transmitted through the opening at an angle for ophthalmological treatment of the tissue that is positioned posterior of the mask. The light that is reflected via the reflective material may be delivered from a broad area light source, such as a VCSEL or an LED.

The reflective material may be deposited on an inner surface of the at least one transparent opening or the reflective material may be disposed within a lens component that is positioned within the at least one transparent opening. The lens component may be an active component such that a relative position of the reflective material within the at least one transparent opening is adjustable in order to adjust the angle of the reflected light that is transmitted through the at least one transparent opening. This process may be similar to a gonio lens reflection. The reflective material may be disposed or oriented at a pre-selected angle within the at least one transparent opening such that the reflected light is incident on the Schlemm's canal. The angle of the reflected light may be greater than 30 degrees, such as between 30 and 120 degrees.

In some embodiments, the mask may be configured for use with a spacer that is positioned between the mask and a light source in order to separate the mask from the light source. The spacer may have a proximal end and a distal end that is opposite the proximal end. The proximal end of the spacer may be coupleable with the light source and the distal end of the spacer may be in alignment with the mask. The spacer may be made of a transparent material (such as free-space) that exposes at least a portion of the mask to the therapeutic light that is delivered from the light source.

The mask, spacer, and light source may be components of a light therapy system, which may also include a control unit that is operably coupled with the light source to control the delivery of therapeutic light to the tissue of the eye in an automated manner. The control unit may be configured to control the light source in order to deliver a series of pulses of the therapeutic light to the tissue. Each pulse of the series of pulses may be sufficient to induce therapeutic healing of target tissue without causing traditional photocoagulation of the tissue. In other embodiments, the control unit may be configured to control the light source to deliver a single pulse or flash of the light to the tissue. The single pulse or flash may be sufficient to induce therapeutic healing of the tissue.

In some embodiments, the mask includes a plurality of openings (e.g., between 1 and 100 openings and more commonly between 5 and 40 transparent openings) in which each opening is positioned radially outward relative to the limbus of the eye. In such embodiments a reflective material is typically positioned within each transparent opening to reflect light that is transmitted through each transparent opening at an angle relative to an initial direction of travel of the light. A light source may be used to simultaneously irradiate each transparent opening. Each transparent opening may have an opening diameter of between 1 and 1000 microns, between 10 and 1000 microns, and more commonly between 100 and 600 microns.

In other embodiments the transparent opening may be an elongate or annular slot that is positioned radially outward relative to the limbus of the eye. The reflective material may be positioned along at least a portion of the elongate or annular slot to reflect light that is transmitted through the elongate or annular slot at an angle, or the reflective material may be positioned along an entire length of the elongate or annular slot. The mask may also include a reflective material that is positioned on the outer surface of the mask that reflects light away from the outer surface of the mask. The mask may be made of a transparent material and may be rendered opaque due to the reflective material that is positioned on the outer surface of the mask. The transparent opening(s) may be etched or formed in the reflective material.

According to another aspect, a lens for treating an eye of a patient is provided. The lens is positionable on the eye of the patient and includes an inner surface that is positionable against the eye and an outer surface that is opposite the inner surface. A reflective material is disposed within the lens. The reflective material is configured to reflect treatment light that is transmitted through the lens at an angle for ophthalmological treatment of the eye tissue that is off-axis from an axis of the treatment light. The lens is typically optically opaque to prevent transmission of the treatment light through the lens and the lens typically includes at least one transparent opening that allows transmission of the treatment light through the at least one transparent opening. The reflective material may be disposed within the at least one transparent opening.

The reflective materials may be deposited on an inner surface of the at least one transparent opening or the reflective material may be disposed within a lens component that is positioned within the at least one transparent opening. The lens component may be an active component such that a relative position of the reflective material within the at least one transparent opening is adjustable in order to adjust the angle of the reflected light that is transmitted through the at least one transparent opening. The reflective material may be disposed or oriented at a pre-selected angle within the lens such that the reflected treatment light is incident on the Schlemm's canal. The angle of the reflected treatment light may be greater than 30 degrees, such as between 30 and 120 degrees.

According to another aspect, a method for treating an eye of a patient using a light based system is provided. The method includes positioning a lens on a surface of the eye, in which lens includes an inner surface, an outer surface that is opposite the inner surface, and a reflective material that is disposed within the lens. The method also includes aligning a light source relative to the lens and delivering therapeutic light from the light source toward the lens so that at least a portion of the delivered therapeutic light irradiates the reflective material and is reflected by the reflective material at an angle toward tissue within the eye that is off-axis from an axis of the therapeutic light delivered from the light source. In a specific embodiment, the therapeutic light that irradiates the reflective material is reflected toward tissue of the Schlemm's canal of the eye.

The angle of the reflected therapeutic light may be greater than 30 degrees, such as between 30 and 120 degrees. The lens may be optically opaque to prevent transmission of the therapeutic light through the lens and the lens may include at least one transparent opening that allows transmission of the therapeutic light through the at least one transparent opening. The reflective material may be disposed within the at least one transparent opening. The reflective materials may be deposited on an inner surface of the at least one transparent opening or the reflective material may be disposed within a lens component that is positioned within the at least one transparent opening. In some embodiments, the lens component may be an active component and the method may include adjusting a relative position of the reflective material within the at least one transparent opening in order to adjust the angle of the therapeutic light that is transmitted through the at least one transparent opening.

Embodiments of the disclosure covered by this patent are defined by the claims below, not this summary. This summary is a high-level overview of various aspects of the disclosure and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

BRIEF DESCRIPTION OF THE DRAWINGS

Further details, aspects, and embodiments of the disclosure will be described by way of example only and with reference to the drawings. In the drawings, like reference numbers are used to identify like or functionally similar elements. Elements in the figures are illustrated for simplicity and clarity and have not necessarily been drawn to scale.

FIGS. 14 and 15 illustrate exemplary embodiments of masks or lenses that include a material that converts light to electrical energy and that may be employed to direct therapeutic light onto target tissue within the eye.

FIG. 16 illustrates a method of converting light energy to electrical power via a mask or lens.

DETAILED DESCRIPTION OF THE DISCLOSURE

Figure 1A:
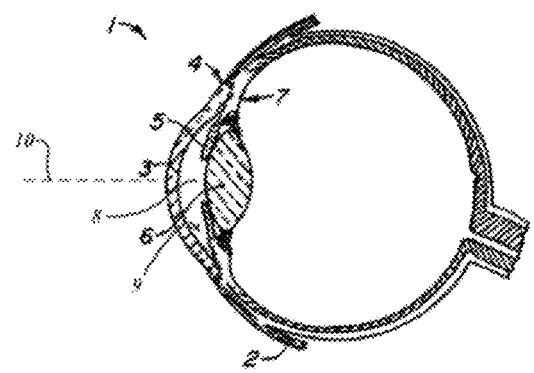
FIG. 1A shows the anatomy of an eye with relevant parts labeled to provide anatomical references.

Conventional ophthalmic laser systems generally require a laser console and a laser probe where the laser console contains the laser source, power supply and controller. The laser probe generally contains an optical fiber and connector for attachment to the laser console. The laser console is typically an AC powered system, placed on a surface that is at least several feet away from a patient's eye, and the laser output light from the console is typically transported by an optical fiber (i.e., waveguide) to the patient's eye where photocoagulation based treatment may take place. Such a system typically requires external AC power, a long multi-mode fiber to bring light to the end applicator that could be implemented with a slit lamp adapter, a scanner, or a handheld contact probe.

Conventional ophthalmic laser systems also employ a single light source such as an edge emitting diode laser, diode pumped solid state laser, or fiber laser. The distal end of the laser probe typically touches the surface of the eye, with the laser source releasing pulsed energy at each spot before being moved to a different spot in a clockwise or counterclockwise rotation around the edge of the eye, which gives rise to the term "cyclophotocoagulation" for treating an eye. The manual process of moving a laser probe over the surface of an eye may be prone to issues such as scratching the surface of the eye. In addition, it is difficult to precisely control the location and positioning of the probe about the eye and thus, it is difficult to precisely control the delivery the laser light to the eye, which may lead to inconsistent treatment.

The embodiments described herein provide certain advantages and improvements over standard ophthalmic laser systems. For example, the ophthalmic laser systems described herein do not require the use of a traditional laser console, the use of a traditional treatment probe, or the use of an expensive optical waveguide. Rather, the systems herein employ an optical eye mask or lens that is positioned atop the eye and that is operative with a light source to provide the therapeutic treatment. The lens or eye mask is a single use, disposable component that includes openings or slots that are disposed around the cornea or limbus when the lens or eye mask is placed on the eye. The use of the lens or eye mask eliminates or greatly minimizes many of the issues associated with conventional laser probes, such as scratching of the eye surface and inconsistency in delivery of the treatment light. The systems described herein may also employ less expensive and complicated light sources to provide the therapeutic treatment. For example, a broad area light source may be used that irradiates the entire area of the eye rather than individual spots or points of the eye. As used herein, the term "broad area" means the light source has a large optical near field aperture in contrast to a single mode laser that has a very small near field aperture typically on the order of the laser wavelength. For example, broad area light sources may produce a light spot that covers most of the lens or eye mask or the entire lens or eye mask, which is in contrast to conventional treatment procedures the produce a small light spot (e.g., single or multi-mode laser spot) that is focused within the eye. Broad area light sources are typically lower in cost and are more reliable due to thermal management being less challenging. The broad area light sources do not require precise beam control as is required with conventional laser treatment probes. The broad area light source also does not have to be a laser source, or stated differently, non-laser sources may be employed in the light based systems described herein. The systems herein may also include an appropriate spacer to create a distance between the light source and the eye.

The systems described herein are not constrained for use with desktop systems and thus, they may be employed remotely from a treatment facility, such as in rural or secluded areas or in a person's home. Furthermore, the treatment provided is more precise and predictable than those achieved with conventional systems. Many embodiments may be particularly designed for transscleral cyclophotocoagulation where energy is directed through selected portions of the pars plicata region to the ciliary body, structures under the scleral layers, and the overlying conjunctiva to treat a glaucomatous eye. Additional features and aspects of the embodiments will be more apparent in reference to the various figures described herein below.

FIG. 1A shows the anatomy of an eye 1 with relevant parts labeled to provide anatomical references. The sclera 2 is a tough sheath around the eye which meets the cornea 3 at a circular junction called the limbus 4. Behind the cornea 3 lies the iris 5, the lens 6 and the ciliary body and related processes 7. The anterior chamber is the fluid-filled compartment within the eye 1 just in front of the pupil 8. Viewed in profile, the anterior chamber is bounded by the domed cornea 3 in front and by the colored iris 5 behind. Where the cornea 3 and the iris 5 converge they form an angle 9 referred to herein as the angle of the anterior chamber. Further eye 1 may have a visual/optical axis 10.

Figure 1B:
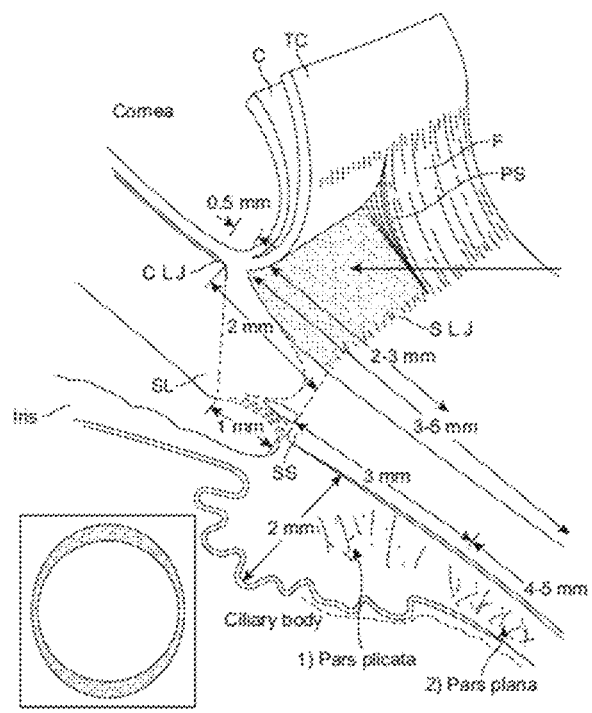
FIG. 1B shows further details of the eye anatomy.

FIG. 1B shows further details of the surgical eye anatomy. Embodiments described herein may target intraocular structures that span from the posterior pars plicata to the pars plana. Alternatively, the pars plana may be targeted and the pars plicata, ciliary body, and other ciliary processes avoided.

Figure 2:
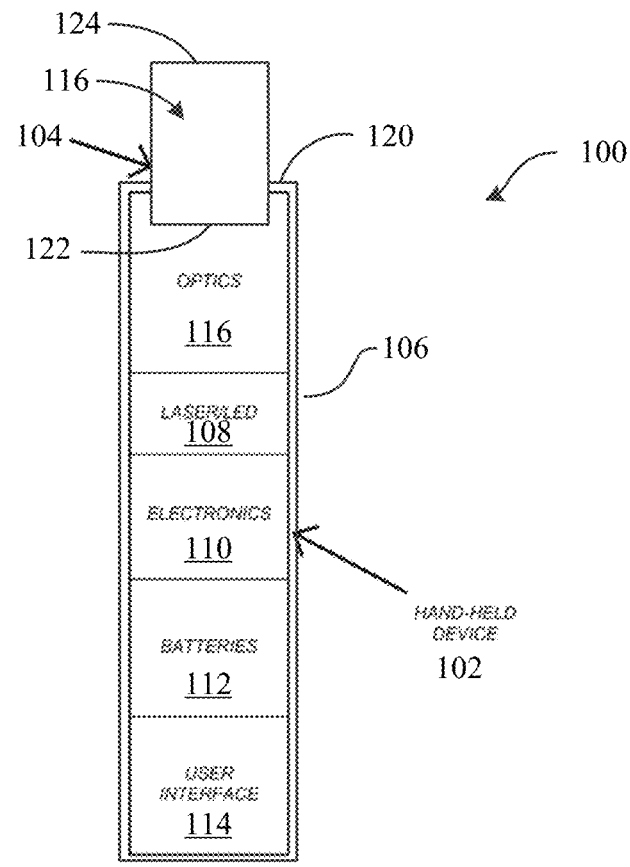
FIG. 2 illustrates an ophthalmic treatment device that may be used to deliver therapeutic light to a lens or eye mask.

FIG. 2 illustrates an ophthalmic treatment device 100 that may be used to deliver therapeutic light to any of the lenses or eye masks described herein (hereinafter mask). Specifically, the ophthalmic treatment device 100 may be used to target the ciliary body and/or pars plana. The ophthalmic treatment device 100 in FIG. 2 is illustrated as a laser probe or handheld device, although it should be realized that the device may be substantially different in other embodiments. For example, the device 100 may not be configured to be grasped and operated by hand, such as by being integrated into a desktop console or workstation. Regardless of the configuration, the ophthalmic treatment device 100 functions to deliver therapeutic light to the mask that is positioned atop the patient's eye.

In FIG. 2, the ophthalmic treatment device 100 comprises a treatment device body 102 and a replaceable, single-use or multi-use tip 104 that is detachably coupled with the treatment device body 102. The treatment device body 102, includes a housing 106 with an exterior surface that defines a handle for grasping by a user. The treatment device body 102 further includes a therapeutic light source 108 that is configured to provide therapeutic light for treatment of the tissue of the eye. The light source 108 is typically positioned within the housing 106, although in some embodiments, the proximal end of the housing 106 may couple with an external light source, or the light source may be positioned externally of the housing 106.

Figure 10:
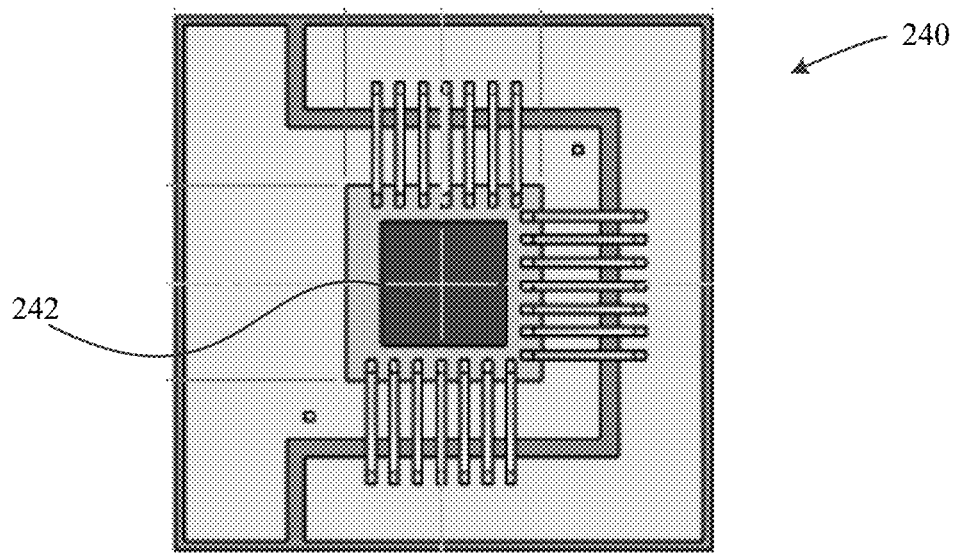
FIG. 10 illustrates a surface emitting laser diode that may be used as a light source to deliver therapeutic light to a patient's eye.

The light source 108 may be a broad area light source that is less expensive than those that are employed in conventional treatment systems, such as laser probes. In an exemplary embodiment, the light source 108 is a vertical cavity surface emitting lasers (VCSELs), a surface emitting LED, or a combination thereof. A VCSEL laser emits a single mode beam that is easier to align with the masks described herein. FIG. 10 illustrates a surface emitting laser diode 240 that may be used in the light source 108. The surface emitting laser diode 240 includes a surface emitting laser 242 that emits a circular beam. The light source 108 may be configured to deliver 1-10 watt 810 nm laser light, which is a light source that is significantly less expensive than those employed in conventional laser treatment probes. A typical VCSEL made with the GaAs/AlGaAs compound semiconductor material could have a lasing wavelength of 780-860 nm depending on the aluminum content and the vertical cavity length.

The use of a VCSELs or surfacing emitting LED provides several advantages over light sources that are used in conventional systems, such as edge emitting lasers. For example, VCSELs emit a symmetric, circular beam, that is typically contained in an angle of approximately 15 degrees. Such a beam can be easily collimated onto the mask that is positioned on the patient's eye. The use of the mask, however, allows virtually any light source to be used, including edge emitting lasers. Since the ophthalmic treatment device 100 of the instant application may employ broad area light sources, the ophthalmic treatment device 100 does not require the use of any optical fibers and thus, the system may be entirely free of optical fibers and the components that are associated therewith. In some embodiments, the light source 108 and/or ophthalmic treatment device 100 may be operative with an RFID reader, a camera, an image processing unit, and the like. The RFID reader may be employed to enforce a single use of one or more of the components described herein, such as the tip 104, the mask, and the like.

The light source 108 may include a single light emitting device or an array of such devices that each independently deliver a beam of therapeutic light. The array of light emitting devices in combination may produce a beam of light that is emitted from the distal end of the ophthalmic treatment device 100 toward the mask that is positioned on the surface of the eye. In some embodiments, each light emitting device of the array may be independently controlled so that only a single light emitting device, or a portion of the light emitting devices, is delivering the therapeutic light at a given time. In this manner, the treatment that is delivered to the eye may be varied and controlled in a desired manner.

The treatment device body 102 may also include one or more additional components. For example, the treatment device body 108 may include lens optics 116. As illustrated in FIG. 2, the lens optics 116 may be positioned within the housing 106 while in other embodiments the lens optics 116 may be part of the single-use or multi-use tip 104 (also referred to herein as a spacer 104). In yet other embodiments, the lens optics 116 may be split between the housing 106 and the single-use or multi-use tip 104. In some embodiments, the use of the mask and broad area light source eliminates the need for lens optics 116 to be employed, since the mask directs treatment light within the eye is a desired manner.

The treatment device body 102 may also include a control unit or electronics 110 that control the delivery of the therapeutic light in an automated manner. The treatment device body 102 may also include one or more batteries 112, an AC/DC power supply, and/or a user interface 114. The ophthalmic treatment device 100 may be used to deliver therapeutic light to target tissue of the eye in a variety of different methods. The user interface 114 may comprise one or more mechanical dials, buttons, or switches that may be used to adjust parameters of the therapeutic light source with or without a touchscreen or a dedicated electronic display. Additionally or alternatively, treatment parameters may be communicated to the probe via radio frequency, e.g., Bluetooth.

Eye Mask

Figure 3:
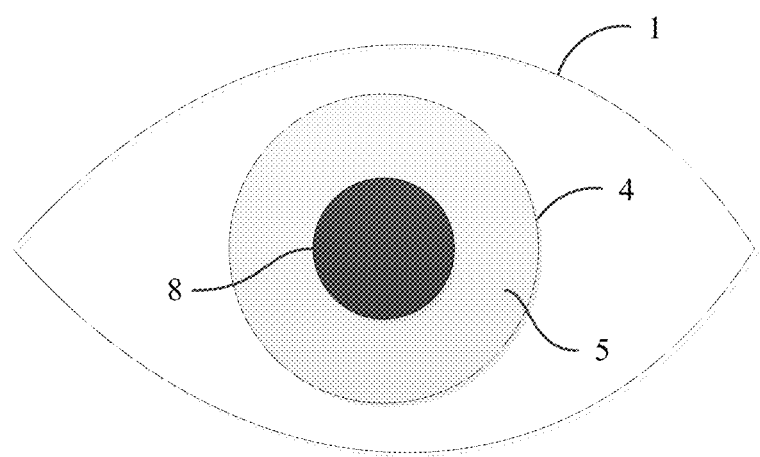
FIG. 3 illustrates a schematic drawing of an eye.
Figure 4A:
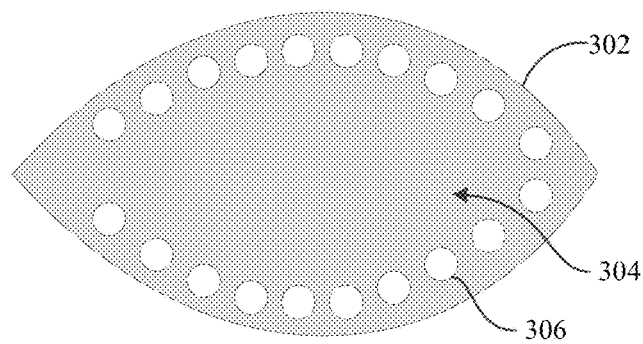
FIGS. 4A and 5A illustrate lenses or eye masks that may be employed to direct therapeutic light onto target tissue within the eye.
Figure 4B:
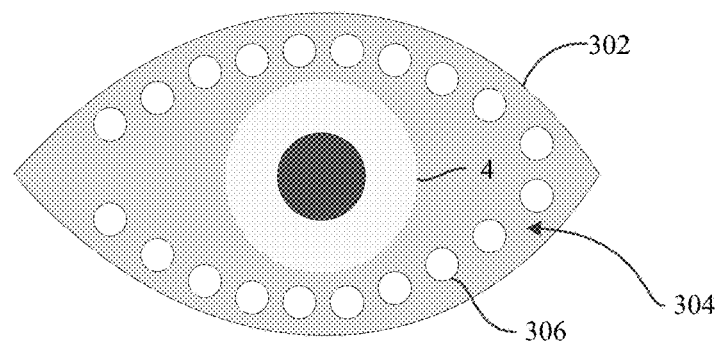
FIGS. 4B and 5B illustrate the lenses or eye masks of FIGS. 4A and 5A superimposed on the eye of FIG. 3.
Figure 5A:
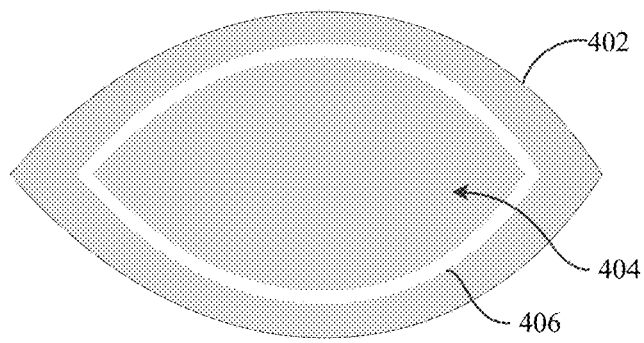
Figure 5B:
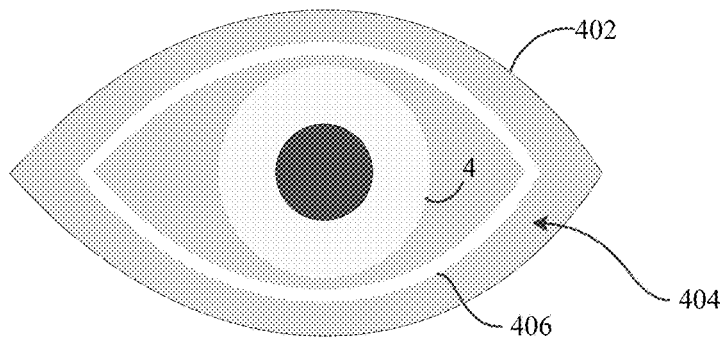

FIG. 3 illustrates a simplified front view of an eye 1. Specifically, FIG. 3 illustrates the pupil 8, the iris 5, and the limbus 4 of the eye 1. FIGS. 4A and 5A illustrate embodiments of masks that may be employed to direct the therapeutic light onto target tissue within the eye. FIGS. 4B and 5B illustrates the masks superimposed on the eye of FIG. 3. The use of the masks of FIGS. 4A and 5A eliminate the need for the treatment device to define the beam that is employed in treating the tissue of the eye. For example, in conventional devices, a distal end of the treatment device, which is typically a laser probe, must be properly positioned on the surface of the patient's eye. Proper positioning of the treatment device on the surface of the eye typically involves orienting the treatment device relative to the eye so that an emitted beam of light contacts the eye at a desired angle. The emitted beam of light must also be properly oriented, which often requires the use of collimators, diodes, and/or waveguides.

The use of the masks of FIGS. 4A and 5A eliminate the need for such alignment and orientation of the treatment device since the individual masks define and direct the treatment light onto and within the eye. Rather, proper positioning of the eye mask typically only involves centering of the eye mask relative the cornea. As such, the treatment process is substantially less dependent on the light source and/or treatment device for precise control and delivery of the treatment beam, which eliminates the need for beam alignment components such as collimators, diodes, waveguides, and the like.

Referring specifically to FIG. 4A, illustrated is an mask 302 that includes a body 304 and a plurality of openings or apertures 306. The body 304 is typically made of a thin material that is biologically compatible with the eye so as not to cause discomfort or irritation to the eye during use. Exemplary materials include polymethyl methacrylate, oxygen-permeable polymers, pliable hydrophilic plastics (e.g., hydrogels), and the like. The body 304 includes an inner surface that is positionable against the surface of the eye and an outer surface that is positioned opposite of the inner surface.

The body 304 of the mask 302, or at least a portion thereof, is optically opaque in order to prevent light from being transmitted through the mask 302. In an exemplary embodiment, the entire body 304 of the mask 302 is optically opaque, although an entirely optically opaque body 304 is not required. The optically opaque body 304 prevents the therapeutic light, or other light, from being transmitted through the mask 302 to sensitive tissue of the eye (e.g., retina) that may be damaged by such light. The body 304 is also typically reflective so that light that is incident upon the body 304 is reflected away from the mask 302. The reflective function of the body 304 ensures that the body 304 does not absorb, or minimally absorbs, incident light, which prevents the mask 302 from overheating due to exposure to the therapeutic light or any other light. As such, the mask 302 may remain relatively cool and comfortable to the user.

In some embodiments, the mask 302 may be made of an opaque material. In other embodiments, the mask 302 may be made of a transparent material and an opaque material may be coated or formed on the inner and/or outer surface of the mask 302. The reflective characteristic is typically achieved by coating, forming, or otherwise positioning a reflective material on the outer surface of the mask 302. For example, a metallic material may be coated, formed, or positioned atop the mask to provide the reflective characteristics. In an exemplary embodiment, the reflective material that is coated, formed, or positioned atop the mask is the same material that renders the mask 302 opaque. The reflective material may be coated, formed, or positioned atop the entire outer surface of the mask 302, or atop only a portion of the outer surface of the mask 302 as desired.

The mask 302 includes a plurality of transparent openings 306 that allow light to traverse, transmit, or penetrate through the mask 302. Each opening 306 is positioned radially outward from a center of the mask 302. As shown in FIG. 4B, the openings 306 are positioned about the mask 302 so that when the mask 302 is positioned on the eye 1, each opening 306 is positioned radially outward of the limbus 4 of the eye 1, commonly along the sclera. The iris 5 and pupil 8 of the eye 1 are entirely covered by the optically opaque body 304. In FIG. 4B, the openings 306 entirely surround the eye 1, although various other opening configurations could be used as desired. The openings 306 allow the therapeutic light that is delivered from the light source 108 (e.g., VCSEL, LED light, and the like) to penetrate through the body 304 and to the underlying target tissue of the eye 1 for treatment.

The openings 306 by formed in the material that is coated, formed, or otherwise positioned on the outer and/or inner surface of the mask 302. For example, the openings 306 may be etched in the reflective and/or opaque material coating of the mask 302. In other instances, a template or pattern could be employed in coating or forming the reflective and/or opaque material on the mask 302. The template or pattern could aid in proper placement of the openings 306 about the mask 302 and/or aid in preventing the reflective and/or opaque material from coating or covering the openings 306. In an exemplary embodiment, the openings may be between 100 and 600 microns in diameter, although various other opening diameters may be employed. The mask 302 typically includes between 1 and 100 openings, 5 and 40 openings, and more commonly between 10 and 25 openings, although other configurations are possible. In a specific embodiment, the mask 302 includes approximately 18 openings, which provides a treatment pattern that corresponds to an existing treatment protocol. The arrangement of the openings illustrated in FIGS. 4A and 4B allows a laser treatment procedure to be performed in a manner similar to conventional cyclophotocoagulation procedures.

Referring now to FIG. 5A, illustrated is another mask 402 that may be employed in delivering therapeutic light to the eye 1. The mask 402 includes a body 404 that is also typically made of a thin biologically compatible material as previously described. The body 402 is optically opaque and typically includes a reflective material as previously described. Instead of a plurality of openings, however, the mask 402 includes a transparent slot 406 that allows the therapeutic light to penetrate or be transmitted through the body 404. The transparent slot 406 may be formed via etching or through the use of a template/pattern as previously described, or may be formed via any other method. As shown in FIG. 5B, the transparent slot 406 is positioned about the mask 402 so that when the mask 402 is positioned on the eye 1, the transparent slot 406 is positioned radially outward of the limbus 4, commonly along or adjacent the sclera. The iris 5 and pupil 8 of the eye 1 remain entirely covered by the optically opaque body 404. The transparent slot 406 allows the therapeutic light that is delivered from the light source 108 (e.g., VCSEL, LED light, and the like) to penetrate through the body 404 and to the underlying target tissue of the eye 1 for treatment.

In some embodiments, the transparent slot 406 may have a slot width of between 50 µm and 600 µm, although various other slot widths may be employed. In addition, although the transparent slot 406 is illustrated as a continuous slot or feature, in other embodiments, the transparent slot 406 may include only a single slot or multiple disconnected sections as desired. In other embodiments the transparent slot 406 may be positioned only on one side of the eye 1, such as above or below the iris 8. The transparent slot 406 may be configured and arranged to provide a desired treatment to a portion of the eye.

In some embodiments, the masks, 302 and 402, of FIGS. 4A and 5A may be include or be operative with an RFID, a memory chip, a special mechanical attachment mechanism, and the like. The use of an RFID may allow the ophthalmic treatment device 100 to recognize the configuration of the masks, such as whether the mask includes transparent openings and/or slots and/or the size and arrangement of these features, and to adjust the parameters of the light source 108 based on the specific configuration of the mask being employed. The memory chip may store this information and deliver it to the ophthalmic treatment device 100. The RFID and/or memory chip may also be used to ensure that the mask is only used a single time. The special mechanical attachment mechanism or feature may enable the mask to releasably couple or attach to the distal end of a spacer, such as that illustrated in FIG. 11. The special mechanical attachment mechanism may aid in a rough alignment of the spacer and mask.

It should be realized that the masks, 302 and 402, of FIGS. 4A and 5A are for illustrative purposes and are not meant to limit the exact configuration of the mask described herein and that various other configurations may be employed. For example, an mask may include a combination of transparent slots and openings as desired, or may include other geometric shapes, such as squares, rectangles, ovals, polygons, and the like.

Figure 9:
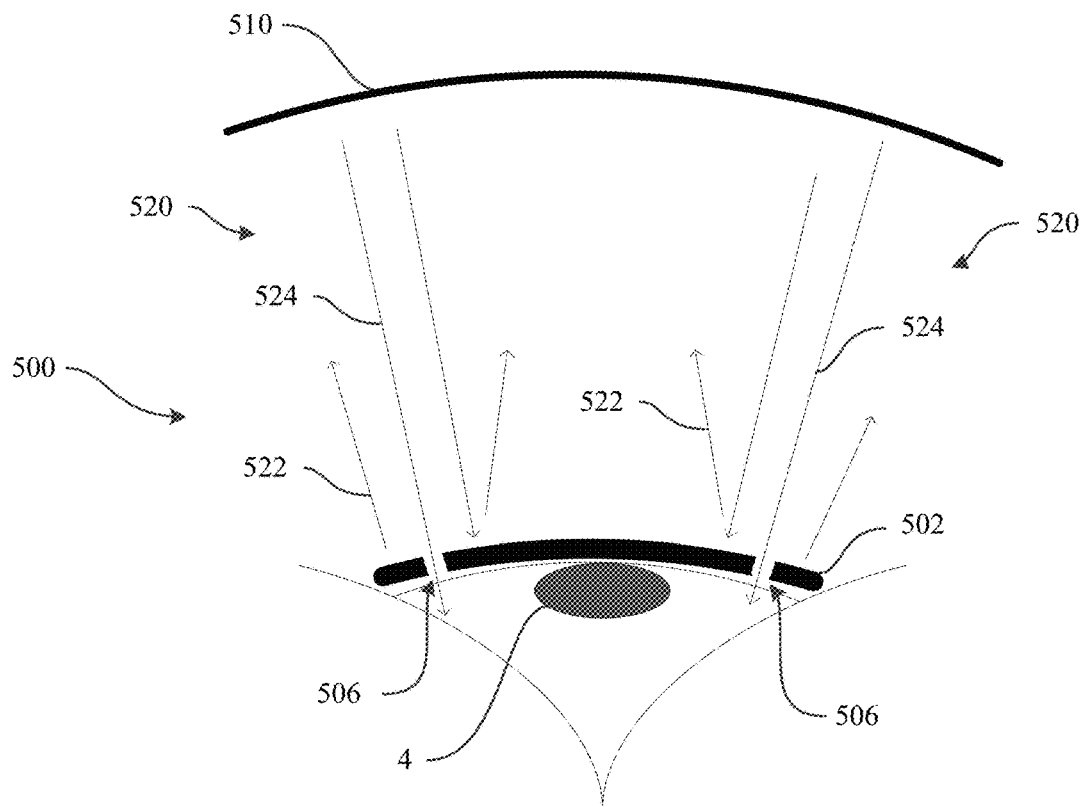
FIG. 9 illustrates a system that employs a lens or eye mask in combination with a light source that delivers therapeutic light to a patient's eye.

Referring now to FIG. 9, illustrated is a system 500 that employs an mask 502 in combination with a light source 510 that delivers therapeutic light to a patient's eye 1. The mask 502 of FIG. 9 represents the mask 302 of FIG. 4A, the mask 402 of FIG. 5A, or any other mask that may be used in the treatment process. Similarly, the light source 510 may be the light source 108 of the ophthalmic treatment device 100 or any other light source that is used in the treatment process. As described herein, the mask 502 is positioned about the eye so that the transparent feature(s) 506 (e.g., openings and/or slot) is positioned outward of the limbus 4 of the eye 1.

The light source 510 delivers therapeutic light 520 toward the mask 502. The light source 510 is positioned relative to the mask 502 so that the light source 510 simultaneously irradiates at least a portion of the mask and at least one or more transparent feature(s) 506. In the illustrated embodiment, the light source 510 simultaneously irradiates the entire mask 502 and each of the transparent features 506. As described herein, the light source 510 may include a single light emitting device or an array of light emitting devices. If an array of light emitting devices is employed, the delivery of a therapeutic light beam from each light emitting device may be controlled to simultaneously irradiate the mask 502 or to irradiate the mask 502 in a varied manner as desired. The light source 510 is typically communicatively coupled with a control unit that is programmed to control the delivery of therapeutic light to target tissue of the eye 1 in an automated manner.

The mask 502 includes a reflective and/or opaque material. The reflective material causes some of the therapeutic light 520 to be reflected 522 away from the mask 502. The reflective material may be a reflective coating or layer that is disposed on the outer surface of the mask. The reflective and/or opaque material ensures that the therapeutic light 520 is only delivered to the desired target tissue of the eye 1. The transparent features 506 allow a portion 524 of the therapeutic light 520 to traverses, transmit, or penetrate through the mask 502 to target tissue that is positioned immediately below or behind the transparent features 506. Since the light source 510 simultaneously irradiates some or each of the transparent features 506, the light source 510 simultaneously treats the target tissue associated with the irradiated transparent features 506.

In some embodiments, the transparent features 506 may be configured to direct the therapeutic light 524 so that it contacts the eye 1 at a desired angle, which eliminates or minimizes the need for precise alignment of the light source 510 and/or ophthalmic treatment device 100 about the eye. In contrast, conventional treatment systems that employ treatment probes require that the user align the light source and treatment probe about the eye prior to treating the eye. Despite best efforts, user alignment of the treatment probe renders the alignment and orientation of the probe about the eye relatively imprecise. The use of the mask 502 may offer substantially greater precision and control in delivery of the therapeutic light to desired target tissue, since the arrangement, orientation, and positioning of the transparent features 506 about the eye is not subject to user alignment. Rather, the arrangement, orientation, and positioning of the transparent features 506 about the eye 1 is controlled by selecting an appropriate mask 502 for use, or custom fabricating the mask 502 to the unique shape and/or other characteristics of the eye. The arrangement, orientation, and positioning of the transparent features 506 is maintained as the mask 502 is positioned and maintained in position atop the eye 1.

Figure 11:
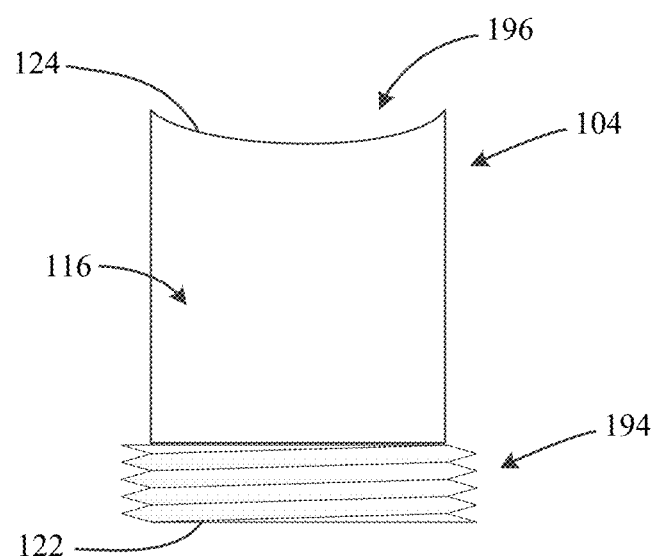
FIG. 11 illustrates an embodiment of a spacer of the ophthalmic treatment device.

Although not illustrated in FIG. 9, a spacer, such as the spacer 104 illustrated in FIG. 11, is typically positioned between the mask 502 and the light source 510 in order to separate the mask 502 from the light source 510. A proximal end of the spacer may be coupled with the light source 510, such as by coupling the proximal end with the ophthalmic treatment device 100, and a distal end of the spacer may be positioned atop the mask 502. In some embodiments, the distal end of the spacer may attach to or couple with the mask 502. The spacer is typically a transparent material that exposes the mask 502 to the therapeutic light delivered from the light source 510.

In some embodiments, the light source 510 may be angled or curved to aid in delivery of the therapeutic light 520. For example, the curvature of the light source 510 or spacer could match the curvature of the eye 1. The contour matching of the light source 510 and/or spacer may allow the therapeutic light 524 to contact and enter the eye 1 at a roughly normal angle (e.g., an incidence angle of the therapeutic light may be within +/−10 degrees of normal). In comparison with conventional devices, the use of the mask 502 and/or light source 510 provides greater control over the angle of the therapeutic light that is incident on the eye 1, since it is difficult for a user of a conventional device (e.g., laser probe) to keep the device properly aligned about the eye at all times. In some embodiments, the ophthalmic treatment device 100 may include optics 116 that are used to angle the therapeutic light 520 so that it is roughly normal to the eye 1.

Figures 6, 7:
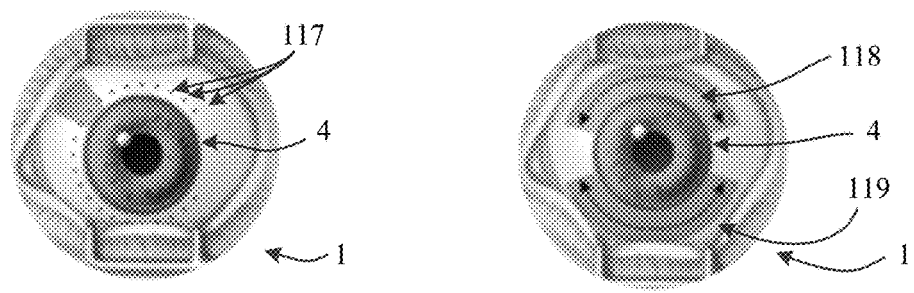
FIGS. 6 and 7 illustrate treatment procedures that may be employed to treat the eye.

FIGS. 6 and 7 illustrate treatment procedures that may be employed to treat the eye. FIG. 6 illustrates a plurality of spaced apart fixed locations 117 about the limbus 4 of the eye that are each treated with therapeutic light. The plurality of spaced apart fixed locations 117 illustrated in FIG. 6 corresponds to the plurality of openings 306 of the mask 302 of FIG. 4A. The treatment of the spaced apart fixed locations 117 is described in U.S. Patent Publication 2010/0076419, which is incorporated herein by reference. In the treatment described in the '419 publication, a laser probe is moved and repositioned about the eye in order to treat each spaced apart fixed location 117 individually. In contrast to this procedure, the treatment procedure described herein simultaneously irradiates and treats some or all of the spaced apart fixed locations 117. In an exemplary embodiment, each of the spaced apart fixed locations 117 is simultaneously irradiated and treated. This eliminates the need and time required to individually treat each spaced apart fixed location 117. The treatment of each spaced apart fixed location 117 is also more precisely defined and controlled since the alignment of the therapeutic beam is not based on a user alignment of a treatment probe about the eye. In delivering the treatment, the therapeutic light may be delivered once to each spaced apart fixed location 117, or may be delivered multiple times to each spaced apart fixed location 117 as described below.

FIG. 7 illustrates another treatment method, in which a treatment probe is slid or swept across target tissue concurrently with the light delivery. The treatment method results in an arcuate or curved pattern of treated tissue, 118 and 119, above and below the limbus 4. This treatment method is described in U.S. Patent Publication 2015/0374539, which is incorporated herein by reference in its entirety. The arcuate or curved pattern of treated tissue, 118 and 119, corresponds with the shape and configuration of the transparent slot 406 of the mask 402 of FIG. 5A. In contrast to the treatment procedure of the '539 publication, the treatment procedure described herein simultaneously irradiates and treats some portion or the entire portion of the arcuate/curved pattern, 118 and 119. In an exemplary embodiment, the entire portion of the arcuate/curved pattern, 118 and 119, is simultaneously irradiated and treated, although the light source may be controlled as described herein to vary the treatment along some portion of the arcuate/curved pattern, 118 and 119, as desired. The treatment procedure described herein eliminates the need and time required to slide or sweep a treatment probe across the surface of the eye. The treatment of the arcuate/curved pattern, 118 and 119, is also more precisely defined and controlled since is does not rely on a user sliding or sweeping a treatment probe across the surface of the eye. In delivering the treatment, the therapeutic light may be delivered once to the arcuate/curved pattern, 118 and 119, or may be delivered multiple times to the arcuate/curved pattern, 118 and 119, as described below.

Figure 8:
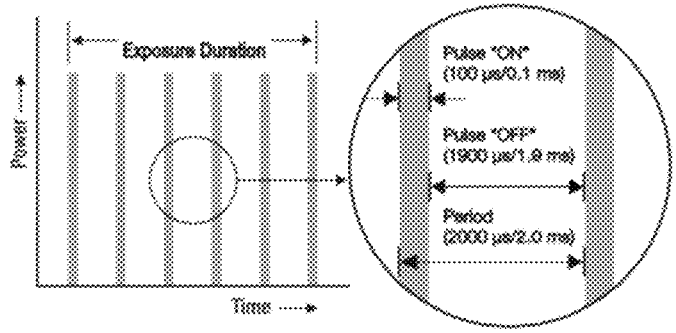
FIG. 8 illustrates exemplary laser parameters for treating an eye.

As briefly described above, the light source 108 and control unit 110 may be configured to deliver light energy in a pulsed or continuous wave emission mode. For example, in some embodiments, the light source 108 and control unit 110 may be configured to operate with a 30% duty cycle, with an "on" time of about 500 μs and an "off" time of about 1100 μs, about a 15% duty cycle, with an "on" time of about 300 μs and an "off" time of about 1700 μs, or about a 10% duty cycle, with an "on" time of about 200 μs and an "off" time of about 1800 μs. Careful selection of the laser energy pulse "on" and "off" times can avoid undesired thermal damage to a target by allowing the target to cool during the "off" time of the laser before the next pulse of energy is delivered during the "on" time. The duty cycle may be selected so that cumulative thermal buildup, caused by insufficient cooling during the "off" time may be avoided. Thus, damage may be reduced to a minimum level sufficient to trigger a biological response needed for lowering of intraocular pressure (IOP). FIG. 8 illustrates an exemplary pulsed mode that may be used in some embodiments of the present invention. The illustrated mode may have an "on" time of 100 μs and an "off" time of 1900 μs with a period of 2000 μs.

FIG. 11 illustrates an embodiment of the spacer 104. Although the spacer 104 may be a single-use component or a multi-use component, in an exemplary embodiment, the spacer 104 is a single-use component that is removable from the housing 106 and that is and replaceable with another spacer 104. The spacer 104 separates the light source 108 and the distal end of the ophthalmic treatment device 100, which may be hot, from the mask (i.e., 302, 402, and 502) and the surface of the eye 1 to ensure that the surface of the eye 1 is not damaged. In an exemplary embodiment, the spacer 104 may be made of a glass mask, a plastic mask, or of any other material employed in forming optics. The spacer 104 may be a hollow of solid body of material as desired and is typically transparent so as not to impede in delivery of the therapeutic light.

The spacer 104 includes a proximal end 122 and a distal applicator end 124 opposite the proximal end 122. The spacer 104 may house or include the optics 116 of the ophthalmic treatment device 100 if any optics 116 are used. The proximal end 122 of the spacer 104 is configured to mechanically couple with the distal end 120 of the housing 106 using one or more engagement features. For example, FIG. 11 illustrates the proximal end 122 of the spacer 104 having a threaded engagement feature 194 that allows the spacer 104 to be rotatably engaged and disengaged with the housing 106, which may include a corresponding threaded engagement feature. The spacer 104 may alternatively include one or more protrusions (not shown) that snap fit within one or more corresponding engagement features of the housing 106, or may include any other male or female connector that engages with a corresponding female or male connector of the housing 106.

As briefly described above, in some embodiments a contact surface 196 of the distal end 124 may be contoured to match the contour of the eye. For example, the contact surface 196 may be concave with a curvature configured to match the curvature of the sclera. The concave configuration of the contact surface 196 may render the contact surface essentially cup shaped with a configuration that corresponds to an average eye geometry. The contoured configuration of the contact surface 196 may aid in delivery of the therapeutic light at an angle that is normal to the surface of the eye. The distal end 124 of the spacer 104 may also be configured to attach or couple with the mask (e.g., 302, 402, 502) or with the eye socket.

In some embodiments, the spacer 104 includes a computer readable media. The computer readable media may be an optical barcode (e.g., 2D barcode), embedded chip (e.g., RFID, NFC, direct read memory chip), and the like. The computer readable media may be read by a corresponding sensor associated with the treatment device body 102. In some embodiments, the computer readable media may be a security feature that protects the treatment device body 102 from being used with unauthorized replacement spacers 104. Optionally, the computer readable media may carry treatment parameter information associated with the spacer 104 and/or mask. For example, a spacer 104 may be coupled with the treatment device body 102 and a sensor of the treatment device body may read the computer readable media to determine which treatment parameters are associated with the type of spacer 104 that is attached thereto and/or mask that is positioned about the eye. Thereafter, the control unit 110 of the treatment device body 102 may be configured to automatically adjust parameters of the light source 108 for the particular treatment and/or mask.

Figure 12:
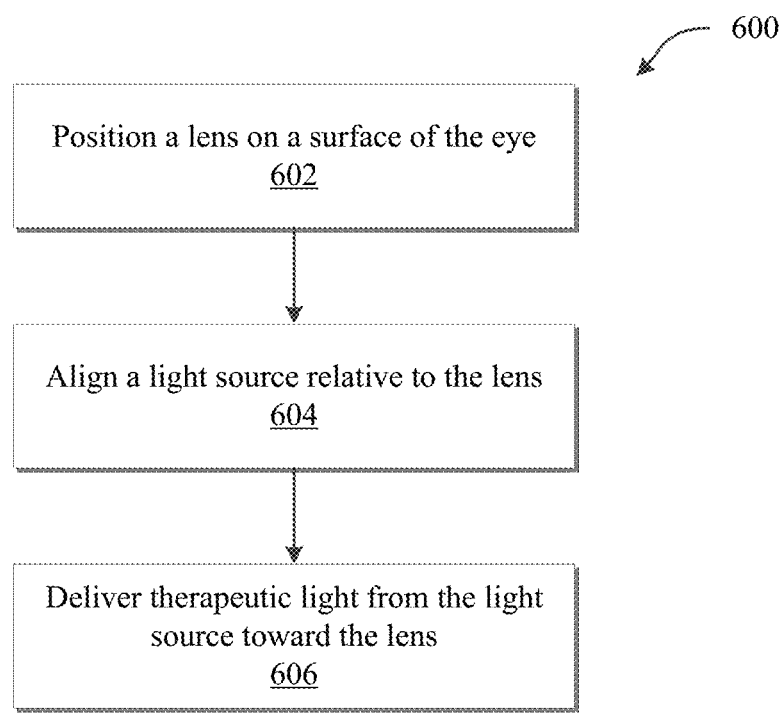
FIG. 12 illustrates a method for treating an eye.

FIG. 12 illustrates a method 600 for treating an eye. At block 602, a lens or mask is positioned on a surface of the eye. The mask includes an inner surface and an outer surface that is positioned opposite the inner surface. The mask is optically opaque to prevent transmission of light through the mask. The mask also includes a transparent opening or slot that allows transmission of light through the optically opaque mask to target tissue of the eye that is positioned behind the transparent opening or slot.

At block 604, a light source is aligned relative to the mask. At block 606, therapeutic light is delivered from the light source toward the mask so that the delivered therapeutic light irradiates at least a portion of the optically opaque mask and irradiates the transparent opening or slot. At least some of the therapeutic light traverses through the transparent opening or slot to the target tissue that is positioned behind the transparent opening or slot. In an exemplary embodiment, the therapeutic light irradiates most or all of the optically opaque mask and irradiates each transparent opening or slot.

The method also typically includes positioning a spacer between the mask and the light source to separate the mask from the light source. The spacer has a proximal end and a distal end that is opposite the proximal end with the proximal end being coupled with the light source and the distal end being positioned atop the mask and/or coupled with the mask. The method typically also includes activating a control unit in order to deliver the therapeutic light from the light source in an automated fashion. In some instances delivering the therapeutic light from the light source in an automated fashion includes delivering a series of pulses of the therapeutic light to the target tissue with each pulse of the series being sufficient to induce therapeutic healing of the target tissue without causing traditional photocoagulation of the target tissues. The description of each pulse being sufficient to induce therapeutic healing without causing traditional photocoagulation means that no visible damage is present on, or associated with, the target tissue, such as blanching of target tissue. In other instances delivering the therapeutic light from the light source in an automated fashion includes delivering a single pulse of the therapeutic light to the target tissue with the single pulse of therapeutic light being sufficient to induce therapeutic healing of the target tissue.

Light Powered Eye Mask

In some embodiments, the eye mask or lens may be configured to convert light to electrical energy. Specifically, the mask may include a material that is configured to convert light to electrical energy so that light that is incident or irradiated on the outer surface of the mask may be used to power one or more electronic components. The material that converts light to electrical power may be a solar cell type material, which may be positioned on the outer surface of the mask, or embedded within the mask material. For ease in describing the embodiments herein, the material that converts light to electrical power will be referred to as a solar cell or solar cell material.

As described herein, the mask may be made of an optically opaque material to prevent transmission of light through the mask, although in other embodiments the mask (or some portion thereof) may be made of a transparent material so that light is able to be transmitted through the lens and to the eye. The solar cell material may be positioned on the opaque portion of the mask so that light that is incident on this portion of the mask is converted into electrical energy. By using a solar cell material to cover the opaque area of the mask, light that is not used for ophthalmic treatment may be converted to electrical power, which may then be used to power electronic components that are useful in providing the treatment. The solar cell material may be made as a part of the mask and may cover the entire area of the treated eye and/or may be substantially larger in area than the size of the light beam. In some embodiments, the solar cell material may cover at least 30 percent of the surface area of the mask, although the solar cell material typically covers at least 40 percent or 50 percent of the surface area of the mask. In some embodiments, the solar cell material may cover more than 60 percent or 70 percent of the surface are of the mask. In a specific embodiment, the solar cell material may cover more than 90 percent of the surface are of the mask. For example, in the embodiment illustrated in FIG. 14, the solar cell material may cover the entire surface area of the mask 702a except where the openings 706a are located, which would result in the solar cell material covering more than 90 percent of the surface area of the mask 702a.

In addition to the greater surface area that the solar cell material may employ, the masks described herein may be capable of generating a significant amount of electrical energy. For example, the incident optical power level on the opaque area of the mask may be substantially higher than conventional transparent lenses since the opaque portion of the mask will block transmission of the light to the eye. The power density for an 810 nm treatment may be estimated to have a treatment threshold of 350 W/cm$^2$ in a typical operation. This power density would give rise to a total incident power on an eye mask having a surface area of 213 mm$^2$ of approximately 745 W—i.e., 350 W/cm$^2$*2.13 cm$^2$. Assuming that the solar cell material covers approximately 50 percent of the mask, the total incident power on the solar cell material would be approximately 372 W—i.e., 745 W/2. If the solar cell material converted the total incident power at 20% rate, the generated electrical power would be approximately 74 W, which represents a substantial increase in power in comparison with conventional lenses having small solar cells. The high available electrical power converted in the opaque area could be used for any ophthalmology applications, in addition to the low power sensor applications associated with a solar cell.

Figure 13:
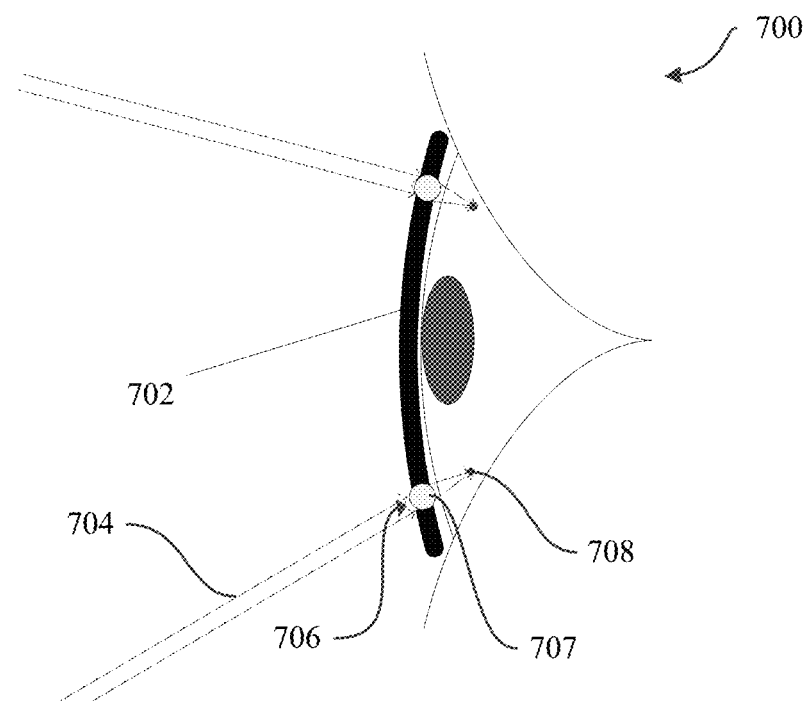
FIG. 13 illustrates an embodiment of a mask or lens that includes a material that is configured to convert light to electrical energy.

FIG. 13 illustrates an exemplary embodiment of a mask 700 that includes a solar cell material 702 that converts light to electrical energy. The mask 700 is positioned about the eye so that the mask 700 covers the entire iris of the eye and so that the edge of the mask extends into the sclera of the eye. The mask 700 is opaque as described herein so that light is prevented from being transmitted through the mask 700. In an exemplary embodiment, the opaque portion of the mask 700 covers the entire iris of the eye and extends into the sclera. As such, when the mask 700 is placed about the eye, the wearer is unable to see through the mask 700. The entire mask 700 may be opaque or only a portion of the mask 700 may be opaque. In either embodiment, however, the opaque portion of the mask 700 typically covers the eye so that the wearer of the mask 700 is unable to see through the mask 700.

The solar cell material is positioned on the optically opaque portion of the mask 700. Since essentially the entire mask 700 is optically opaque, the surface area that the solar cell material may occupy is substantially greater than a similar area of conventional contact lenses, which have large transparent areas that allow transmission of light to the eye. In conventional lenses, the solar cell material is typically not positioned directly in front of the pupil or iris since such positioning of the solar cell material would substantially impede a user's vision by blocking or interfering with transmission of light to the eye. As such, in conventional lenses, the solar cell material and/or any other electronic components are only positioned near the edges of the lens so that the central portion of the lens remains free of such materials. This configuration ensures that the wearer's vision is not negatively impacted by the solar cells. Since the solar cell material is not positioned on the central portion of the lens, this portion of the lens is a dead space to energy conversion, meaning that this portion is unable to contribute to conversion of light to energy.

In contrast, the masks contemplated herein do not suffer from these advantages since the masks are intended to be opaque so that a user cannot see through the mask. Since the masks are opaque, the solar cell material and/or other electronic components may occupy essentially any portion of the mask including the central portion directly in front of the pupil and iris. The masks described herein do not include dead spaces where energy conversion cannot occur, or include considerably smaller dead spaces. Thus, the masks described herein are able to generate considerably more electrical energy than conventional lenses.

As shown in FIG. 13, the mask 700 also includes at least one transparent opening 706 that allows transmission of light 704 through the mask 700. As described in greater detail above, the opening 706 is intended to allow the light 704 to irradiate target tissue 708 of the eye positioned posterior or behind the transparent opening 706. The opening 706 is positioned radially outward from a center of the mask 700 and is typically positioned radially outward of the limbus of the eye, commonly along the sclera as described herein. The light 704 is provided from a therapeutic light source (e.g., light source 108) for treatment of the tissue of the eye. As described herein, the light source may be a broad area light source, such as VCSELs, a surface emitting LED, or a combination thereof.

FIGS. 14 and 15 illustrate embodiments of masks, 702a and 702b, that may be employed in treating an eye of a patient. The masks, 702a and 702b, illustrate different arrangements of openings that may be used on a mask. The masks, 702a and 702b, of FIGS. 14 and 15 are for illustrative purposes and it should be recognized that the arrangement, number, and/or orientation of the openings may be modified as desired. FIG. 14 illustrates a plurality of openings 706a that are arranged in a circular or oval pattern around the central portion of the mask 702a. The openings 706a may have a similar arrangement pattern, orientation, and/or hole size as the mask illustrated in FIG. 4A. The arrangement of the openings illustrated in FIG. 14 allows a laser treatment procedure to be performed in a manner similar to conventional cyclophotocoagulation procedures. FIG. 15 illustrates a mask 702b that includes a relatively large opening 706b having a circular shape and an arrangement, orientation, and/or opening size similar to the mask illustrated in FIG. 5A. The arrangement of the opening 706b illustrated in FIG. 15 allows a laser treatment procedure to be performed in a manner similar to that described in FIGS. 5A-B.

FIGS. 14 and 15 also illustrate a treatment beam or spot 712 irradiated on the respective masks, 702a and 702b. The treatment beam or spot 712 has a diameter that is larger than a diameter of the opening(s), 706a and 706b, so that the opening(s), 706a and 706b, are simultaneously irradiated. In some embodiments, the treatment beam or spot 712 may have a diameter that is smaller than the mask, 702a and 702b, so that the entire treatment beam or spot 712 is enclosed within the outer periphery of the mask, 702a and 702b, although in other embodiments the treatment beam or spot 712 may be larger than the mask, 702a and 702b.

The treatment beam or spot 712 covers the central portion of the mask, 702a and 702b, and irradiates the solar cell material, which is positioned on the opaque portion of the mask, 702a and 702b, including on the central portion of the mask directly in front of the iris and/or pupil as described herein. The solar cell material converts the light into electrical energy, which is used to power one or more electronic components 710 that are positioned on the mask, 702a and 702b. Exemplary electronic components 710 are described in greater detail below. As illustrated in FIGS. 14 and 15, the electronic components may be positioned on the outer edge of the mask, 702a and 702b, although in other embodiments, one or more of the electronic components may be positioned on or near the central portion of the mask. Since the central portion of the mask, 702a and 702b, is opaque, positioning the electronic component on or near the mask's central portion does not impede or obscure a wearer's vision by blocking light that would otherwise travel through the mask. Positioning the electronic components 710 on or near the central portion may enable the electronic components 710 to function in a more efficient manner depending on the operation being performed.

In some embodiments, a passive or active optical component may be embedded or positioned in one or more of the opening(s), 706a and 706b, of the respective mask, 702a and 702b. In an exemplary embodiment, each of the openings, 706a and 706b, may have a passive or active optical component. The passive or active optical components may interact with the light that is transmitted through the respective opening in which the passive or active optical component is positioned. The use of the passive or active optical component may greatly enhance the control, performance, and/or delivery of the light to the target tissue positioned behind the mask, 702a and 702b, which may greatly enhance the therapeutic benefit that is achievable with the mask.

The electronic components 710 that may be used with the mask include a sensor, a MEMS device, a wireless signal transceiver, a power detector, an imaging device, an optical power detector, and the like. The sensor may be a pressure sensor such as an intraocular pressure sensor, a chemical sensor such as glucose sensor, a bio-material sensor, and the like. For example, a pressure sensor may be used to measure the intraocular pressure (IOP). The pressure sensor may employ one or more strain gauges that are used to measure the IOP. A glucose sensor may also be used that is able to measure the blood sugar level of the wearer. The glucose sensor may employ a photo-acoustic sensor that is capable of measuring glucose levels.

The higher power that is able to be generated by the solar cell may enable additional sensors and/or more complex sensors to be employed in comparison with conventional lenses. Stated differently, the number of sensors and/or the operations of the sensors are not as limited as sensors employed in conventional lenses due to the increased electrical energy that the masks described herein are able to generate. Accordingly, additional or enhanced treatments and/or therapeutic data of the patient may be measured by the masks described herein. Similarly, additional treatment options may be available due to the additional electrical energy that is generated.

In some embodiments, the electronic components 710 may include a processing component (i.e., microprocessor). The processing component may be employed to analyze data that is measured by the sensor(s). In some embodiments, the data may be analyzed in real time to adjust one or more parameters of the treatment process being delivered. For example, a sensor may be positioned on the mask and the sensor may be used to measure an amount of irradiance of treatment light that contacts the mask. The processing component may analyze the data to determine a light energy that is being delivered to the target tissue of the eye. The processing system may transmit this information to an external component and/or use this information to adjust the power level of the treatment light in order to optimize the treatment that the patient is receiving. As such, the sensor and processing component may be used to estimate the actual power or energy that is delivered to the eye in a significantly more accurate manner than conventional systems. In this manner, the use of the sensor(s) and microprocessor allow for a closed loop feedback system to be employed in delivering the therapeutic treatment. Conventional treatment systems are incapable of estimating the actual power that is incident on the eye. Rather, these systems often measure the irradiance of the light as the light exits the light source, which may differ from the irradiance of light that is incident on the eye.

The active or passive optical components that are disposed within the openings of the mask could be used to form or condition the treatment light that is transmitted through the openings. The active or passive optical components could be nano or micro optical components. The passive or active components may include a microlens, a micro-electro-mechanical system (MEMS) mirror or component, a combination of a microlens and MEMS mirror/component, and the like. The energy that is generated by the solar cell material may power the passive or active optical components. When a microlens is employed, the microlens can perform beam forming optical tasks, such as focusing light to a sub-sclera location for glaucoma treatment. The microlens may be electronically controllable in order to focus the light on a desired spot within the eye. The microlens may minimize scattering of the treatment light and may concentrate the treatment beam to a desired area within the eye. FIG. 13 illustrates a microlens 707 disposed within the opening 706 of the mask 702. The microlens 707 is used to focus input light 704 to a spot 708 below the sclera surface. The use of the microlens may enable a more targeted and exact delivery of the treatment light to the target tissue within the eye. The use of the microlens may also enable a more precise and proper orientation of the treatment beam relative to the eye. In some embodiments, multiple masks could be employed with each mask having a slightly different opening size and/or focal length that is achieved via the microlens disposed within the opening. The use of the multiple masks may allow a specific mask to be selected based on the individual features of the patient and/or the specific treatment that is provided.

The active optical elements, such as a MEMS mirror, can provide several functions that may improve the therapeutic treatment provided. For example, the MEMS mirror can function as an on/off light switch within the opening 706 to regulate and control the transmission of treatment light 704 through the opening 706. The on/off switch function may be used to limit the delivery of treatment light to sensitive areas of the eye, may be used to provide the circular treatment pattern that is described in relation to FIGS. 4A and 4b, and/or may be used to provide the series of short duration pulses that are sufficient to induce therapeutic healing without causing traditional photocoagulation. To provide any or all of these treatments, some of the active optical elements may be switched off while other active optical elements are switched on and vice versa. The use of the active or passive optical elements with the mask may greatly enhance the treatment that may be achieved with the mask.

Referring to FIG. 16, a method of converting light energy to electrical energy via a mask or lens is provided. At block 802, a lens or mask that is positionable on an eye is provided. The lens/mask includes an inner surface, an outer surface that is opposite the inner surface, and a material that is configured to convert light to electrical energy (e.g., solar cell material). The solar cell material is arranged on the lens/mask so that light that is incident on at least a portion of the lens/mask is converted to electrical energy. At block 804, the lens is irradiated with light so that at least a portion of the light is converted to electrical energy via the solar cell material. In some embodiment, the solar cell material covers at least 50 percentage of the surface area of the lens/mask.

In some embodiments, at least a portion of the lens/mask is optically opaque in order to prevent transmission of light through the lens. In such embodiments, the solar cell material is positioned on the optically opaque portion of the lens. The lens/mask typically includes at least one transparent opening that allows transmission of light through the lens/mask to target tissue of the eye that is positioned behind or posterior of the at least one transparent opening. The lens/mask may include a passive or active optical component that is embedded in the at least one opening to interact with the light that is transmitted through the at least one opening. The passive or active optical component may be a sensor, a MEMS mirror, a wireless signal transceiver, a power detector, and the like. The lens/mask may also include an electronic component. At block 806, the electronic component is powered via the electrical power produced by the lens/mask.

Reflective Eye Mask

In some embodiments, a reflective optical component, such as a micro mirror, may be positioned in one or more openings of the eye. The reflective optical component may be used to change the direction or angle of the light beam that is transmitted through the opening in order to treat tissue of the eye that is relatively difficult to irradiate or access with conventional treatment probes and systems. For example, the reflective optical component may reflect the light beam at an angle so that the light is able to irradiate tissue within the eye that is not able to be irradiated with conventional systems. The light may be provided by a broad area light source as described herein (e.g., VCSEL, LED, and the like) or may be provided by any other light source that is effective at treating tissue within the eye.

In a specific embodiment, the reflective optical component may be used to treat the Schlemm's canal, which is a lymphatic-like vessel within the eye that aids in regulating aqueous humor levels within the eye via the trabecular meshwork or pathway. The Schlemm's canal is a small area of tissue that allows the aqueous humor to be released from the anterior chamber, which may reduce the intraocular pressure (TOP) within the eye. An irregular functioning of the Schlemm's canal may result in increased TOP and/or any health conditions associated therewith, such as an increased risk of glaucoma.

Irradiating the Schlemm's canal with treatment light may stimulate the Schlemm's canal and/or trabecular meshwork, which may cause the Schlemm's canal and/or trabecular meshwork to function more normally such as by releasing the aqueous humor from within the eye and/or regulating fluidic flows within the eye. Irradiating the Schlemm's canal may have other beneficial effects on the Schlemm's canal and/or surrounding tissue. Thus, therapeutic benefits, such as a reduced risk of Glaucoma, may be achieved by treating the Schlemm's canal and/or trabecular meshwork with treatment light.

Figure 17:
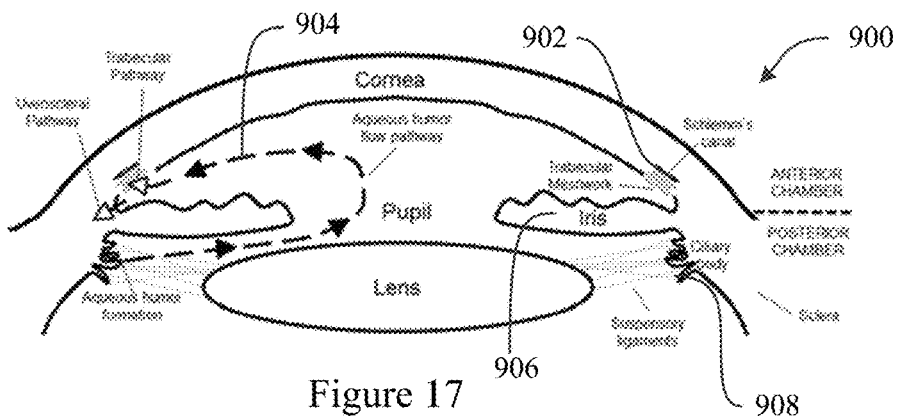
FIG. 17 illustrates a schematic representation of the eye.

FIG. 17 illustrate a schematic representation of the eye 900. The Schlemm's canal 902 is illustrated within the anterior chamber of the eye 900 above the iris 906. FIG. 17 illustrates a fluidic flow 904 of the aqueous humor within the eye between the posterior chamber and the anterior chamber. As illustrated, the aqueous humor flows 904 from the ciliary body 908, where the aqueous humor is produced, to the Schlemm's canal 902 where the aqueous humor is released or drained via the trabecular meshwork or pathway. An increase in TOP within the eye may result from the ciliary body 908 producing more aqueous humor than the Schlemm's canal 902 can release or drain, which may increase the risk for glaucoma and/or other conditions. Traditional attempts to regulate TOP have been focused on treating the ciliary body 908 to reduce the production of the aqueous humor within the posterior chamber. In addition to the treatment of the ciliary body 908, or as an alternative to such treatment, it may be possible to treat the Schlemm's canal 902 to increase the release or drainage of the aqueous humor from within the anterior chamber eye.

The Schlemm's canal 902 is typically ring shaped with a very small width (e.g., roughly 50 microns). The Schlemm's canal 902 is also positioned in an area that is difficult to irradiate or access with treatment light of conventional treatment systems. For example, the Schlemm's canal 902 is off-axis from an axis of conventional treatment probes, which means that the treatment light from conventional treatment probes must be bent or angled by a substantial amount (e.g., 30 degrees or more) in order to irradiate the Schlemm's canal 902. Conventional treatment probes and systems often employ optic fibers that are unable to bend or angle the treatment light at such sharp angles since the optical fibers will typically either break or the light will leak from the optical fiber. Due to the location of the Schlemm's canal 902, it is extremely difficult to treat the Schlemm's canal 902 with conventional treatment systems.

Figure 18:
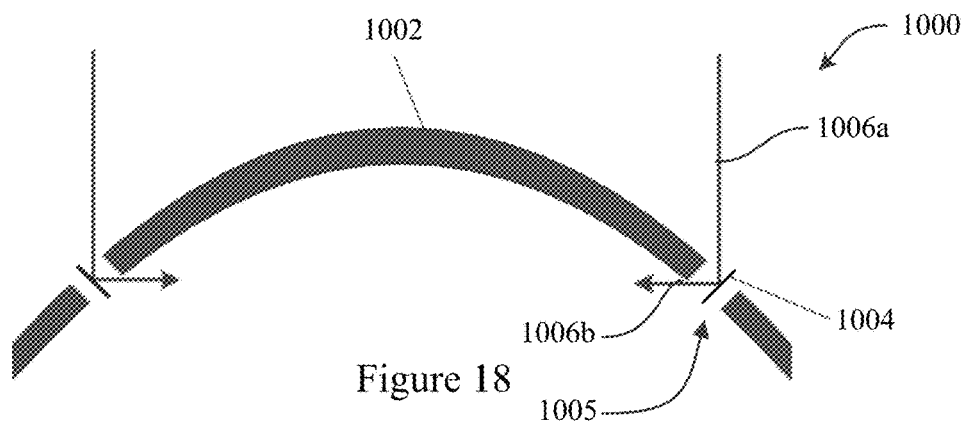
FIG. 18 illustrates a mask or lens that may be used to treat tissue within the eye that is difficult to irradiate.

FIG. 18 illustrates a mask 1000 that may be used to treat tissue within the eye 900 that is difficult to irradiate and/or access, such as the Schlemm's canal 902. The mask 1000 may be a disposable lens or material that is designed for single use. The mask 1000 typically includes an opaque material 1002 or outer surface and at least one opening 1005 as previously described. The opaque material 1002 may be reflective as previously described to minimize heating of the mask 1000. The arrangement and/or orientation of the opaque portion 1002 of the mask 1000 and the opening(s) 1005 of the mask 1000 may be similar to the mask arrangements and/or orientations described in relation to FIGS. 4A-4D, 11, and/or 12. Similarly, the orientation and/or arrangement of the mask 1000 about a user's eye may be similar to the arrangement and/or orientation described in relation to those Figures. For example, the mask 1000 is typically configured so that the opaque portion 1002 of the mask 1000 entirely covers the iris and pupil of the eye and so that the opening(s) 1005 are positioned radially outward of the limbus of the eye as described herein. The mask 1000 is also typically larger in area than a spot size of the treatment light beam.

A reflective component or material 1004 (hereinafter reflective component 1004) is positioned within the at least one opening 1005 of the mask 1000. The reflective component 1004 reflects an input treatment beam at an angle so that the treatment beam is able to access and irradiate tissue that would otherwise be inaccessible. For example, FIG. 18 illustrates a first path 1006a of the treatment beam prior to contacting the reflective component 1004 and a second path 1006b of the treatment beam after contacting the reflective component 1004. As illustrated, the path of the treatment beam is angled, bent, or otherwise altered by a significant amount. In the illustrated embodiment, the treatment beam is angled via the reflective component 1004 by about 90 degrees, although in other embodiments the reflective component 1004 may be used to angle the treatment light by between 15 and 120 degrees, between 30 and 120 degrees, or more commonly between 30 and 90 degrees or between 30 and 60 degrees.

When the mask 1000 has a plurality of openings 1005 similar to the arrangement illustrated in FIGS. 4A and 11, a reflective component 1004 may be positioned within some of the openings 1005 or within each of the openings 1005 as desired. In an exemplary embodiment, each opening 1005 of the plurality of openings 1005 includes a reflective component 1004. Each reflective component 1004 may be orientated within the respective opening 1005 so that the treatment light is reflected radially inward toward the center of the eye to treat target tissue, such as the Schlemm's canal. When the mask 1000 has a single opening 1005 similar to the arrangement illustrated in FIGS. 5A and 12, the reflective component 1004 may be a continuous ring mirror or component that is positioned within the single opening 1005. The continuous ring mirror may be orientated and configured to reflect the treatment light radially inward toward the center of the eye to treat target tissue, such as the Schlemm's canal.

In some embodiments, the reflective component 1004 may be a passive or static component that is designed to angle the treatment light at a preselected, predefined, and/or non-adjustable angle. In other embodiments, the reflective component 1004 may be an active or dynamic component that is able to alter or adjust the angle of the treatment light as desired. As described herein, the reflective component 1004 may be formed by plating or depositing a reflective material on an inner surface or edge of the opening 1004. In other embodiments, a passive or active mirror may be positioned within the opening 1004. The mirror may be positioned or formed on a MEMS device or component in order to allow the orientation of the mirror to be adjusted within the opening 1005 of the mask 1000.

As described herein, the mask 1000 may include a material that is configured to convert light to electrical energy (e.g., solar cell material) so that light that is incident or irradiated on the outer surface of the mask 1000 is converted to electrical energy. The mask 1000 may also include one or more electronic components (e.g., sensors and the like) that are employed in delivering the therapeutic treatment to target tissue within the eye. Accordingly, the various features disclosed in all previous embodiments are applicable to and/or may be employed with the mask 1000 illustrated in FIG. 18. The electrical energy that is generated via the solar cell material may be used to power the reflective component 1004, such as to adjust an orientation of the reflective component 1004 within the opening 1005 and thereby adjust the angle of the treatment light being delivered to the target tissue. For example, the generated electrical energy may be used to control the orientation of a MEMS device or component upon which a mirror or reflective material is positioned or formed.

Figure 19:
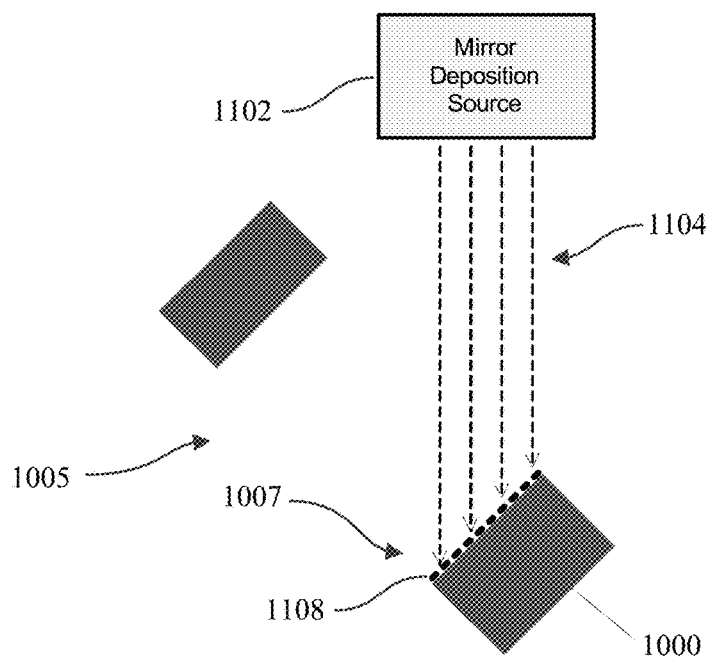
FIG. 19 illustrates an embodiment of forming a reflective material on a surface of an opening of a mask or lens.

FIG. 19 illustrates an embodiment of forming a reflective material on a surface of the opening 1005 of the mask 1000. As illustrated a mirror deposition source 1102 may provide a reflective material 1104 (e.g., aluminum) that is directed toward an inner surface 1007 of the opening 1005 of the mask 1000. The reflective material 1104 may be deposited within the opening 1005 so that a layer 1108 of the reflective material 1104 is formed on the inner surface 1007. The layer 1108 of reflective material 1104 may form or define a reflector that functions to angle the treatment light as described herein. In some embodiments, the reflective material 1104 may form a layer 1108 on the inner surface 1007 without forming a similar layer on the opposite surface of the opening 1005. In other embodiments a reflective component that is separate from the mask 1000 (e.g., a mirror and/or MEMS component) may be inserted within the opening 1005.

Figure 20:
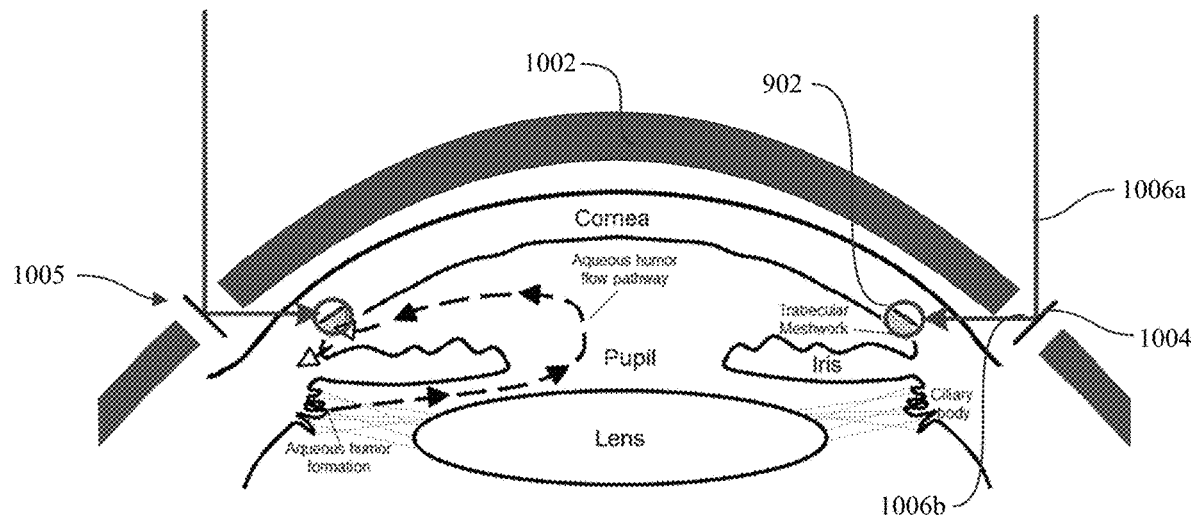
FIG. 20 illustrates the mask or lens of FIG. 18 positioned on the eye schematically represented in FIG. 17.

FIG. 20 illustrates a schematic of the mask 1000 with the inner surface of the mask 1000 positioned on an eye. As illustrated, the opaque and/or reflective portion 1002 of the mask 1000 entirely covers the iris so that the treatment light is substantially prevented from contacting the retina or other sensitive tissue of the eye that is not targeted for treatment. The reflective component 1004 is orientated within the opening(s) 1005 of the mask 1000 so that the treatment light is reflected and angled from a first path 1006a to a second path 1006b in order to treat target tissue within the eye that is off-axis from an axis of the treatment light and/or that is otherwise inaccessible or extremely difficult to irradiate with treatment light. In the illustrated embodiment, the target tissue is the Schlemm's canal 902 and/or trabecular meshwork, although the target tissue may be any other tissue that is identified for irradiation.

The reflective component 1004 may be a reflective material that is deposited on an inner surface of the opening(s) 1005, or the reflective component 1004 may be a mirror or reflective lens that is positioned within the opening(s) 1005. The reflective component 1004 may have a pre-selected angle or orientation within opening(s) 1005 so that the reflected light is directed toward and irradiates the target tissue (e.g., Schlemm's canal). In a specific embodiment, the reflective component 1004 may be an active component that is adjustable so that a relative position or orientation of the reflective component 1004 within the respective opening 1005 is adjustable in order to adjust the angle of the reflected light that is transmitted through the opening. The angle of the reflected treatment light may be greater than 30 degrees, such as between 30 and 120 degrees. The use of the reflective component 1004 within the opening(s) 1005 at the surface of the eyeball may enable the surface of the eyeball to be used as a physical reference to compute an appropriate beam deflection angle for the treatment light.

In treating the Schlemm's canal, the position of the Schlemm's canal can be detected via an image of the eye (e.g., optical coherence tomography (OCT)). With this information, an appropriate mask 1000 may be selected in order to irradiate the Schlemm's canal. For example, a mask 1000 having an appropriately oriented ring shaped mirror may be selected and used to ensure that the treatment light will be reflected toward and irradiate the Schlemm's canal. The use of the ring shaped mirror may enable simultaneously treatment of essentially all of the Schlemm's canal. In another embodiment, the orientation of an active reflective component (e.g., mirror or reflective MEMS component) may be set in order to ensure that the treatment light will be reflected toward and irradiate the Schlemm's canal. The use of the active reflective component may enable the orientation of the reflector(s) to be adjusted in real time to ensure that the Schlemm's canal is being irradiated and treated. The active reflective component may be remotely controlled and locally powered by the solar cell material that is positioned on the opaque area 1002 of the mask 1000. In other embodiments, the locally generated electrical energy may be used to power one or more sensors that aid in determining an effect of the irradiation of the Schlemm's canal, such as by measuring the IOP. The mask 1000 enables the treatment light beam to be effectively guided or directed toward the Schlemm's canal, which is not achievable with conventional laser treatment probes or systems.

Figure 21:
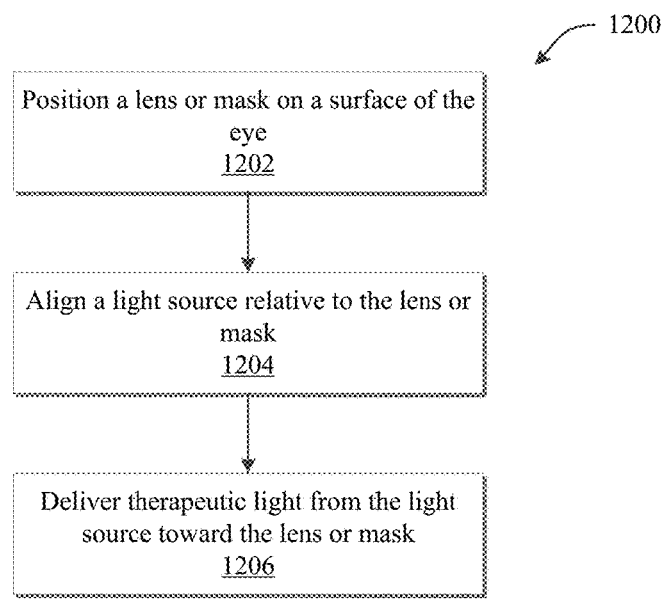
FIG. 21 illustrates a method for treating an eye of a patient using a reflective light based system.

Referring now to FIG. 21, illustrated is a method 1200 for treating an eye of a patient using a reflective light based system. At block 1202, a lens/mask is positioned on a surface of the eye. The lens/mask has an inner surface, an outer surface that is opposite the inner surface, and a reflective material that is disposed within the lens/mask. At block 1204, a light source is aligned relative to the lens/mask. At block 1206, therapeutic light is delivered from the light source toward the lens/mask so that at least a portion of the delivered therapeutic light irradiates the reflective material and is reflected by the reflective material at an angle toward tissue within the eye that is off-axis from an axis of the therapeutic light delivered from the light source. As described herein, the therapeutic light may be reflected by the reflective material toward tissue of the Schlemm's canal of the eye. The angle of the reflected therapeutic light may be greater than 30 degrees, such as between 30 and 120 degrees.

The lens/mask is typically optically opaque to prevent transmission of the therapeutic light through the lens/mask. In such instances, the lens/mask includes at least one transparent opening that allows transmission of the therapeutic light through the at least one transparent opening. The reflective material is disposed within the at least one transparent opening of the lens/mask. In some embodiments, the method 1200 may include depositing the reflective material on an inner surface of the at least one transparent opening. In other embodiments, the reflective material may be disposed within a lens component that is positioned within the at least one transparent opening. In such embodiments, the lens component may be an active component and the method may further include adjusting a relative position of the reflective material within the at least one transparent opening in order to adjust the angle of the therapeutic light that is transmitted through the at least one transparent opening.

One or more computing devices may be adapted to provide the desired functionality described herein by accessing software instructions rendered in a computer-readable form. When software is used, any suitable programming, scripting, or other type of language or combinations of languages may be used to implement the teachings contained herein. However, software need not be used exclusively, or at all. For example, some embodiments of the methods and systems set forth herein may also be implemented by hard-wired logic or other circuitry, including but not limited to application-specific circuits. Combinations of computer-executed software and hard-wired logic or other circuitry may be suitable as well.

Embodiments of the methods disclosed herein may be executed by one or more suitable computing devices. Such system(s) may comprise one or more computing devices adapted to perform one or more embodiments of the methods disclosed herein. As noted above, such devices may access one or more computer-readable media that embody computer-readable instructions which, when executed by at least one computer, cause the at least one computer to implement one or more embodiments of the methods of the present subject matter. Additionally or alternatively, the computing device(s) may comprise circuitry that renders the device(s) operative to implement one or more of the methods of the present subject matter.

Any suitable computer-readable medium or media may be used to implement or practice the presently-disclosed subject matter, including but not limited to, diskettes, drives, and other magnetic-based storage media, optical storage media, including disks (e.g., CD-ROMS, DVD-ROMS, variants thereof, etc.), flash, RAM, ROM, and other memory devices, and the like.

The subject matter of the present invention is described here with specificity, but the claimed subject matter may be embodied in other ways, may include different elements or steps, and may be used in conjunction with other existing or future technologies.

This description should not be interpreted as implying any particular order or arrangement among or between various steps or elements except when the order of individual steps or arrangement of elements is explicitly described. Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

What is claimed is:

1. A light based system for treating an eye of a patient, the light based system comprising:
    an eye mask that is configured for positioning on the eye of the patient, the eye mask having an inner surface that is positionable against the eye and an outer surface that is opposite the inner surface, the eye mask being optically opaque and reflective so that light that contacts the eye mask is reflected away from the outer surface of the eye mask, the eye mask comprising a plurality of transparent openings that allow light to traverse through the eye mask, the plurality of transparent openings being positioned about the eye mask so that when the eye mask is positioned on the eye of the patient, each transparent opening is positioned radially outward relative to a limbus of the eye so that an iris and pupil of the eye remain covered by the optically opaque eye mask; and
    a light source that is configured to deliver therapeutic light toward the eye mask, the light source being positioned relative to the eye mask so that the light source irradiates at least a portion of the eye mask and the plurality of transparent openings such that a portion of the therapeutic light traverses through the plurality of transparent openings to target tissue within the eye.

2. The light based system of claim 1, wherein the eye mask comprises between 1 and 100 openings, and wherein each opening is circular in shape having a diameter of between 10 and 1000 microns.

3. The light based system of claim 1, wherein at least one transparent opening of the plurality of transparent openings comprises an elongate or annular slot, and wherein the light source irradiates the elongate or annular slot.

4. The light based system of claim 1, further comprising a spacer that is positioned between the eye mask and the light source so as to separate the eye mask from the light source, the spacer having a proximal end and a distal end that is opposite the proximal end, the proximal end being coupleable with the light source and the distal end being in alignment with the eye mask, the spacer comprising a transparent material that exposes the at least a portion of the eye mask to the therapeutic light that is delivered from the light source.

5. The light based system of claim 1, wherein the eye mask comprises a reflective material that is positioned on the outer surface of the eye mask and that reflects light away from the outer surface of the eye mask.

6. The light based system of claim 5, wherein the plurality of transparent openings are etched or formed in the reflective material.

7. The light based system of claim 1, further comprising a control unit that is operably coupled with the light source to control the delivery of therapeutic light to the target tissue of the eye in an automated manner.

8. The light based system of claim 1, wherein at least one transparent opening of the plurality of transparent openings includes a converging or diverging optical element, as well as a non-beam-forming material.

9. The light based system of claim 1, wherein the light source is a broad area light source such as a light emitting diode (LED) or vertical cavity surface emitting laser (VCSEL).

10. The light based system of claim 1, wherein the eye mask further comprises a material that is configured to convert light to electrical power so that light that is incident on the outer surface of the mask is converted to electrical energy.

11. The light based system of claim 10, wherein the material that is configured to convert light to electrical power is a solar cell material.

12. The light based system of claim 11, wherein the mask further comprises an electronic component that is powered via the electrical power produced by the solar cell material.

13. The light based system of claim 12, wherein the electronic component comprises a sensor, a MEMS mirror, a wireless signal transceiver, or a power detector.

14. The light based system of claim 10, wherein the material that is configured to convert light to electrical power covers at least 50 percentage of a surface area of the eye mask.

* * * * *